United States Patent
Ekdahl et al.

(10) Patent No.: US 12,301,727 B2
(45) Date of Patent: *May 13, 2025

(54) DIALYSIS MACHINE, MEDICAL EQUIPMENT, AND METHODS FOR ESTABLISHING SECURE COMMUNICATION BETWEEN A DIALYSIS MACHINE AND MEDICAL EQUIPMENT

(71) Applicants: BAXTER INTERNATIONAL INC., Deerfield, IL (US); BAXTER HEALTHCARE SA, Glattpark (CH)

(72) Inventors: Olof Ekdahl, Lund (SE); Bo Wennberg, Staffanstorp (SE); Niklas Eklund, Bunkeflostrand (SE); Christian Karlsson, Staffanstorp (SE); Ding Ma, Inverness, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/217,735

(22) Filed: Jul. 3, 2023

(65) Prior Publication Data
US 2023/0353386 A1    Nov. 2, 2023

Related U.S. Application Data

(63) Continuation of application No. 17/750,714, filed on May 23, 2022, now Pat. No. 11,695,572, which is a (Continued)

(30) Foreign Application Priority Data

Jun. 15, 2017    (SE) .................... 1750761-7

(51) Int. Cl.
  *H04L 9/32*    (2006.01)
  *G16H 40/63*    (2018.01)
  (Continued)

(52) U.S. Cl.
  CPC .......... *H04L 9/3247* (2013.01); *G16H 40/63* (2018.01); *H04L 9/085* (2013.01); *H04W 12/037* (2021.01)

(58) Field of Classification Search
  CPC . H04W 12/041; H04W 12/037; H04W 12/50; H04W 12/069; H04W 12/0471;
  (Continued)

(56) References Cited

U.S. PATENT DOCUMENTS 6,282,183 B1 * 8/2001 Harris .................. H04L 9/40
                                               370/338
8,282,829 B2    10/2012 Yu
(Continued)

FOREIGN PATENT DOCUMENTS

EP    0535863    2/1993
EP    2857054    4/2015
(Continued)

OTHER PUBLICATIONS

Jung Minwoo et al., "Interoperability between medical devices using near field Communication"; 2013 International Conference on Information Science and Applications (ICASA), IEEE, Jun. 24, 2013, pp. 1-4.

*Primary Examiner* — Mohammad A Siddiqi
(74) *Attorney, Agent, or Firm* — K&L Gates LLP

(57) ABSTRACT

The present disclosure relates to establishing secure communication between a dialysis machine and medical equipment. In an example, a dialysis machine includes a control unit configured to establish a short-range wireless connection with external medical equipment. The control unit
(Continued)

establishes the short-range wireless connection by causing a user interface to display a prompt to enter a passkey associated with medical equipment, using the received passkey to pair with the medical equipment, and creating a new bonding table or writing to an empty bonding table using the passkey. The control unit is also configured to generate a shared key using the passkey and at least one predetermined criterion and use the shared key to authenticate with the medical equipment. When authentication with the medical equipment is successful, the control unit enables data communication using the short-range connection with the medical equipment.

21 Claims, 12 Drawing Sheets

Related U.S. Application Data continuation of application No. 16/619,728, filed as application No. PCT/EP2018/065661 on Jun. 13, 2018, now Pat. No. 11,343,105.

(60) Provisional application No. 62/519,994, filed on Jun. 15, 2017.

(51) Int. Cl.
  *H04L 9/08* (2006.01)
  *H04W 12/037* (2021.01)

(58) Field of Classification Search
  CPC ..... H04L 9/085; H04L 9/3242; H04L 9/3247; H04L 2209/805; H04L 2209/88; G16H 40/63; G16H 20/17; G16H 40/67
  See application file for complete search history.

(56) References Cited

U.S. PATENT DOCUMENTS

| | | | |
|---|---|---|---|
| 11,343,105 B2* | 5/2022 | Ekdahl | H04L 9/085 |
| 11,695,572 B2* | 7/2023 | Ekdahl | H04W 12/041 |
| | | | 713/176 |
| 2007/0123166 A1* | 5/2007 | Sheynman | H04W 12/50 |
| | | | 455/41.2 |
| 2008/0003997 A1* | 1/2008 | Parkkinen | H04W 12/128 |
| | | | 455/421 |
| 2010/0318578 A1 | 12/2010 | Treu et al. | |
| 2013/0086642 A1* | 4/2013 | Resch | H04L 9/321 |
| | | | 726/4 |
| 2014/0121845 A1 | 5/2014 | Mueller | |
| 2014/0281554 A1* | 9/2014 | Maletsky | H04L 9/3268 |
| | | | 713/175 |
| 2014/0288947 A1 | 9/2014 | Simpson et al. | |
| 2015/0011970 A1 | 1/2015 | Kamen et al. | |
| 2015/0149096 A1 | 5/2015 | Soykan | |
| 2015/0341785 A1* | 11/2015 | Young | A61N 1/37252 |
| | | | 607/60 |
| 2016/0212783 A1* | 7/2016 | Hampapuram | G06F 3/1423 |
| 2016/0261974 A1* | 9/2016 | Arrizza | H04B 5/72 |
| 2017/0065757 A1 | 3/2017 | Tanenbaum | |
| 2017/0093822 A1* | 3/2017 | Gutierrez | H04W 4/80 |
| 2017/0168688 A1 | 6/2017 | Yuds | |
| 2017/0201886 A1* | 7/2017 | Yang | H04W 12/06 |
| 2018/0338330 A1* | 11/2018 | Ledvina | H04W 12/50 |

FOREIGN PATENT DOCUMENTS

| | | |
|---|---|---|
| WO | 2004070995 | 8/2004 |
| WO | 2017053055 | 3/2017 |
| WO | 2016144541 | 9/2019 |

* cited by examiner

_US 12,301,727 B2_

DIALYSIS MACHINE, MEDICAL EQUIPMENT, AND METHODS FOR ESTABLISHING SECURE COMMUNICATION BETWEEN A DIALYSIS MACHINE AND MEDICAL EQUIPMENT

PRIORITY CLAIM

This application is a continuation of U.S. patent application Ser. No. 17/750,714, filed May 23, 2022, now U.S. Pat. No. 11,695,572, which is a continuation of U.S. patent application Ser. No. 16/619,728, filed Dec. 5, 2019, now U.S. Pat. No. 11,343,105, which is a national phase entry of PCT/EP2018/065661, filed Jun. 13, 2018, which claims priority to U.S. Provisional Patent Application No. 62/519,994, filed Jun. 15, 2017 and Swedish Patent Application No. 1750761-7, filed Jun. 15, 2017, the entire disclosures of which are incorporated by reference herein.

TECHNICAL FIELD

The present disclosure relates to a dialysis machine, to external medical equipment and to corresponding methods for establishing an authenticated connection between a dialysis machine and external medical equipment. The present disclosure also relates to a computer program and a computer program product implementing the method.

BACKGROUND

In treatment of patients suffering acute or chronic renal insufficiency, dialysis therapy is employed. Three general categories of dialysis therapy are hemodialysis, HD, peritoneal dialysis, PD, and continuous renal replacement therapy, CRRT.

In hemodialysis, the patient's blood is cleansed by passage through an artificial kidney in an extracorporeal membrane system, incorporated in a dialysis machine.

In peritoneal dialysis, PD, dialyzing fluid is infused into the patient's peritoneal cavity. This cavity is lined by the peritoneal membrane which is highly vascularized. The metabolites are removed from the patient's blood by diffusion across the peritoneal membrane into the dialyzing fluid. Excess fluid, i.e. water is also removed by osmosis induced by a hypertonic dialyzing fluid.

Through these two processes, diffusion and osmotic ultrafiltration, appropriate quantities of solute metabolites and fluid need to be removed to maintain the patient's body fluid volumes and composition within appropriate limits.

CRRT is used as an alternative therapy for patients who are too ill or unstable for standard hemodialysis. It is similar to hemodialysis and makes use of a semipermeable membrane for diffusion and to some extent convection.

Dialyzing fluids, for use in the above-mentioned treatments, have traditionally been provided in sealed, heat sterilized form, ready for use. For example, peritoneal dialysis is typically performed using bags with three different concentration of dextrose. The bags are being delivered to a patient's home as 1 liter to 6 liter bags with different dextrose concentrations and a normal daily consumption is around 8 to 20 liters of fluid.

A typical daily patient consumption of PD dialysis fluid is eight to twenty liters. The fluid is provided in sterilized bags of sizes up to six liters, which are packed into boxes and delivered, e.g., monthly, for use to the patient's home. The boxes of fluid may be cumbersome and heavy for PD patients to handle, and consume a substantial area in a room of their homes. The bags and boxes also produce a relatively large amount of waste disposed of on a weekly or monthly basis.

Sub-systems for an overall peritoneal dialysis, PD, system that creates dialysis solution at the point of use, e.g., at the PD machine have therefore been proposed. PD fluid is delivered directly to the patient's peritoneal cavity. PD fluid therefore needs to have a level of sterilization suitable for being introduced into the patient's peritoneum. PD dialysis fluid is accordingly premixed and sterilized typically prior to delivery to the location of use, usually the patient's home.

Thus, an overall system for dialysis may include three primary components, namely a dialysis machine, a water purifier and a disposable set operating with both the dialysis machine and the water purifier. The dialysis machine is e.g. a PD cycler, a hemodialysis machine or a CRRT machine.

The dialysis machine and the water purifier are typically separate units. However, during operation the dialysis machine and the water purifier need to communicate. The communication is traditionally implemented using a wired interface. However, sometimes it is desirable to use a wireless interface for this communication.

However, wireless interfaces are vulnerable for man in the middle attacks. Furthermore, if standardized communication protocols are used there is also a risk that the water purifier starts to communicate with other devices than the intended external medical equipment.

The dialysis machine may also need to communicate with other kinds of external medical equipment using a wireless interface.

Consequently, there is a need for improved ways of establishing a secure wireless connection between a dialysis machine and an external medical equipment.

SUMMARY

It is an object of the disclosure to alleviate at least some of the drawbacks with existing solutions. It is a still further object to provide a way establishing trusted communication between a dialysis machine and external medical equipment. In some embodiments, it is an object to provide a solution that increases safety during dialysis. A further object is to provide a solution that mitigates synchronization problems in wireless communication between a dialysis machine and external medical equipment.

According to a first aspect, the disclosure relates to a dialysis machine comprising a short-range communication interface and control unit. The control unit is configured to cause the dialysis machine to establish, using the short-range communication interface, a short-range wireless connection between the dialysis machine and external medical equipment, wherein a first shared key is associated with the short-range wireless connection. The control unit is further configured to obtain a second shared key from a set of second shared keys, wherein the set of second shared keys has been generated, in the dialysis machine, using the first shared key, and to generate a first signature, using the obtained second shared key and a dialysis machine system time. The control unit is further configured to send, using the short-range communication interface, to the external medical equipment, an authentication request comprising the generated first signature, and to receive, using the short-range communication interface, from the external medical equipment, an authentication accept comprising a second signature that has been generated in the external medical equipment using external medical equipment system time and a second shared key from a corresponding set of second shared keys. The corresponding set of second shared keys has been generated in the external medical equipment using the first shared key. Furthermore, the control unit is configured to verify the authenticity of the external medical equipment using the second signature.

The exchange of the signatures before using the short-range communication interface for further communication assures that the dialysis machine and the external medical equipment only communicate with other trusted devices. The enhanced security does not require any additional user interaction, as the second shared keys are generated from the first shared key that is used for establishing the short-range wireless connection.

According to some embodiments the control unit is configured to, upon receiving, from the external medical equipment, a response indicating a synchronization error and comprising external medical equipment system time, to re-generate the first signature, using the external medical equipment system time and send, using the short-range communication interface, an authentication request comprising the re-generated first signature to the external medical equipment.

In this way problems associated with a potential time difference between the system time of the dialysis machine and the external medical equipment is mitigated, as both parties use the system time of the external medical equipment.

According to some embodiments the control unit is configured to verify the authenticated connection using the external medical equipment system time and the re-generated signature.

Hence, as the dialysis machine in this case is already aware about a time difference, it may choose to use the external medical equipment system time, that was signaled in the authentication accept, to avoid problems related thereto.

According to a second aspect the disclosure relates to a corresponding method for establishing an authenticated connection between a dialysis machine and external medical equipment.

According to a third aspect, the disclosure relates to external medical equipment comprising a short-range communication interface and control unit. The control unit is configured to cause the external medical equipment to establish, using the short-range communication interface, a short-range wireless connection between the external medical equipment and the dialysis machine. A first shared key is associated with the short-range wireless connection. The dialysis machine comprises a set of second shared keys generated in the dialysis machine from the first shared key. The control unit is further configured to receive, using the short-range communication interface, from the external medical equipment, an authentication request comprising a first signature, wherein the first signature has been generated in the dialysis machine using the dialysis machine system time and a second shared key from a set of second shared keys. Furthermore, the control unit is configured to obtain the second shared key from a corresponding set of second shared keys that has been generated in the external medical equipment from the first shared key and to verify the authenticity of the dialysis machine using the obtained second shared key and external medical equipment system time. Finally, upon successful verification of the authenticity of the dialysis machine, the control unit is configured to cause the external medical equipment to generate a second signature, using a second shared key, from the corresponding set of second shared keys, and a dialysis machine system time to send, using the short-range communication interface, an authentication accept comprising the generated second signature, to the dialysis machine.

According to some embodiments the control unit, of the external medical equipment, is configured to cause the external medical equipment to compare the external medical equipment system time and the dialysis machine system time, and to, upon the dialysis machine system time and the external medical equipment system time differing above a pre-determined amount, send, using the short-range communication interface, a response indicating a synchronization error and comprising the external medical equipment system time. Then the control unit is further configured to cause the external medical equipment to receive, from the dialysis machine, an authentication request comprising a re-generated first signature that has been re-generated using the external medical equipment system time, using the short-range communication interface.

According to a fourth aspect the disclosure relates to a corresponding method in external medical equipment for establishing an authenticated connection between a dialysis machine and external medical equipment.

According to a fifth aspect, the disclosure relates to a computer program, characterized in code means, which when run in a computer causes the computer to execute any of the methods described above and below.

According to a sixth aspect, the disclosure relates to computer program product including a computer readable medium and a computer program, wherein said computer program is included in the computer readable medium.

According to a seventh aspect, the disclosure relates to system comprising the dialysis machine and the external medical equipment.

BRIEF DESCRIPTION OF THE FIGURES

Embodiments of the disclosure are described in more detail with reference to attached figures illustrating examples of embodiments of the disclosure in which.

DETAILED DESCRIPTION

Figure 1:
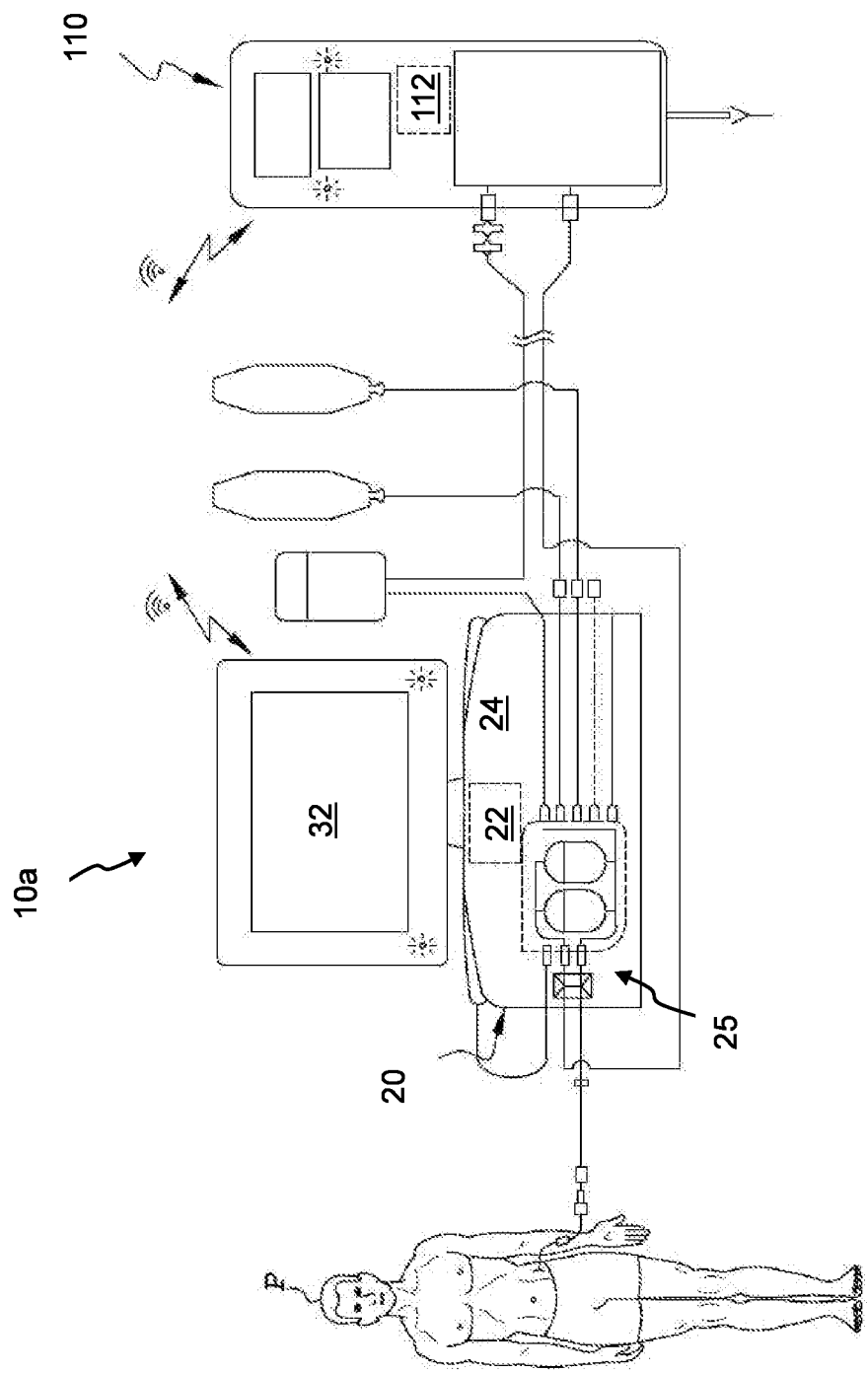
FIG. 1 is a front elevation view of a peritoneal dialysis system comprising a PD cycler and a point of use water purifier where the proposed technique may be implemented.

Dialysis machines, e.g. PD cyclers, hemodialysis machines or CRRT machines, may include wireless communication devices enabling communication with external medical equipment such as an external water purifier, a blood pressure monitor, scale or another kind of external medical equipment. Such external medical equipment typically comprises a simple display and a simple input device such as a keypad with a few buttons. This is typically desirable from a usability perspective, as medical devices should be easy to use.

Open standards for pairing short-range devices, such as Bluetooth™ typically require authentication exchange based on a shared pass key or PIN code. However, the display and keypad may be so limited that they cannot support the user interactions required for a typical pairing where the pass code is entered on each device (e.g. used between smart phones and PCs). Using the example above, the pairing may instead include that a PIN code displayed on a display of the water purifier may be entered on the key board of the dialysis machine and sent back to the water purifier for verification. From a usability perspective, simple user interaction is anyway typically desirable, even though having a patient enter a separate passcode on each device would be more secure.

However, a consequence of using a pairing procedure with limited user interaction, is that it may not be possible to verify that the correct Bluetooth™ devices are paired. For example, in the example above, there is a risk that other devices may connect to the water purifier and interfere with the dialysis treatment. In addition, when using an open standard, it cannot be assured that the dialysis machine is not paired with unknown medical equipment e.g. from an unknown supplier, which may jeopardize security of the treatment. Furthermore, standardized short-range protocols are also sensitive to man in the middle attacks when the limited display and keypad capability combined with usability requirement for medical device dictates the options in open standards, which don't involve sophisticated user interactions. Hence, totally relying on standard protocols when using wireless communication for medical device may jeopardize safety of the treatment.

It is herein proposed to solve those deficiencies by adding an additional authentication protocol on top of a standard short-range wireless communication bonding protocol, such as the standard Bluetooth™ pairing. The proposed authentication protocol uses a second key that is generated from a first key associated with the short-range wireless connection, e.g. a Bluetooth™ pass key. In order to be able to generate the second key the external medical equipment and the dialysis machine need to know the first key and an algorithm or rule (herein referred to as at least one criterion) that is used for creating the key. Such an algorithm or rule will only be available by devices that are trusted by the dialysis machine. In this way, it can be assured that connection is only established with the correct i.e. trusted devices, as other devices do typically not know the algorithm and input parameters of the algorithm. The added authentication protocol may be implemented using a standard protocol such as Json Web Token. However, special adaptions might be required in order to e.g. mitigate synchronization problems.

In the following a dialysis machine, external medical equipment and a method for for establishing an authenticated connection between a dialysis machine and external medical equipment will be described. Note that the proposed technique will herein be described with reference to a peritoneal dialysis system comprising a PD cycler and a point of use water purifier. However, the disclosure is not limited thereto. It must instead be appreciated that the same technique is applicable to any dialysis machine that needs to establish wireless communication with any external medical equipment.

FIG. 1 is a front elevation view of a peritoneal dialysis system comprising a PD cycler and a point of use water purifier.

Referring now to the figures and in particular to FIG. 1, a peritoneal dialysis system having point of use dialysis fluid production of the present disclosure is illustrated by system 10a. System 10a includes a cycler 20 and a water purifier 110. Suitable cyclers for cycler 20 include, e.g., the Amia® or HomeChoice® cycler marketed by Baxter International Inc. To this end, cycler 20 includes a control unit 22. Control unit 22 further e.g. includes a wired or wireless transceiver 221 (FIG. 5) configured for sending information to and receiving information from a water purifier 110.

The water purifier 110 also includes a control unit 112. The control unit 112 of the water purifier is separate from the control unit 22 of the cycler 20. The control unit 112 also includes a wired or wireless transceiver 1221 (FIG. 5) for sending information to and receiving information from control unit 22 of cycler 20.

The cycler 20 includes a housing 24, which holds components 25 programmed via control unit 22 to prepare fresh dialysis solution at the point of use, pump the freshly prepared dialysis fluid to patient P, allow the dialysis fluid to dwell within patient P, then pump used dialysis fluid to a drain. In one embodiment, the components 25 programmed via control unit 22 to prepare fresh dialysis solution at the point of use includes components for a pneumatic pumping system, comprises but is not limited to (i) one or more positive pressure reservoir, (ii) one or more negative pressure reservoir, (iii) a compressor and a vacuum pump each under control of the control unit 22, or a single pump creating both positive and negative pressure under control of the control unit 22, for providing positive and negative pressure to be stored at the one or more positive and negative pressure reservoirs, (iv) plural pneumatic valve chambers for delivering positive and negative pressure to plural fluid valve chambers, (v) plural pneumatic pump chambers for delivering positive and negative pressure to plural fluid pump chambers, (vi) plural electrically actuated on/off solenoid pneumatic valves under control of the control unit 22 located between the plural pneumatic valve chambers and the plural fluid valve chambers, (vii) plural electrically actuated variable orifice pneumatic valves under control of the control unit 22 located between the plural pneumatic pump chambers and the plural fluid pump chambers, (viii) a heater under control of the control unit 22 for heating the dialysis fluid as it is being mixed in one embodiment, and (viii) an occluder under control of the control unit 22 for closing the patient and drain lines in alarm and other situations.

The water purifier 110 includes water purification components, such as one or more reverse osmosis units, an electro-deionization unit (optional), one or more pumps to move water within the water purifier and one or more heater to heat the water within the water purifier. The water purifier 110 also includes at least one reservoir for holding a quantity of water to be purified and for mixing with an anti-bacterial growth agent if provided. The water purifier 110 may also include a deaerator for removing air from the water being purified. The water purifier 110 may further include or operate with pretreatment device, e.g., a water softener module, connected to the water purifier 110.

Figure 2A:
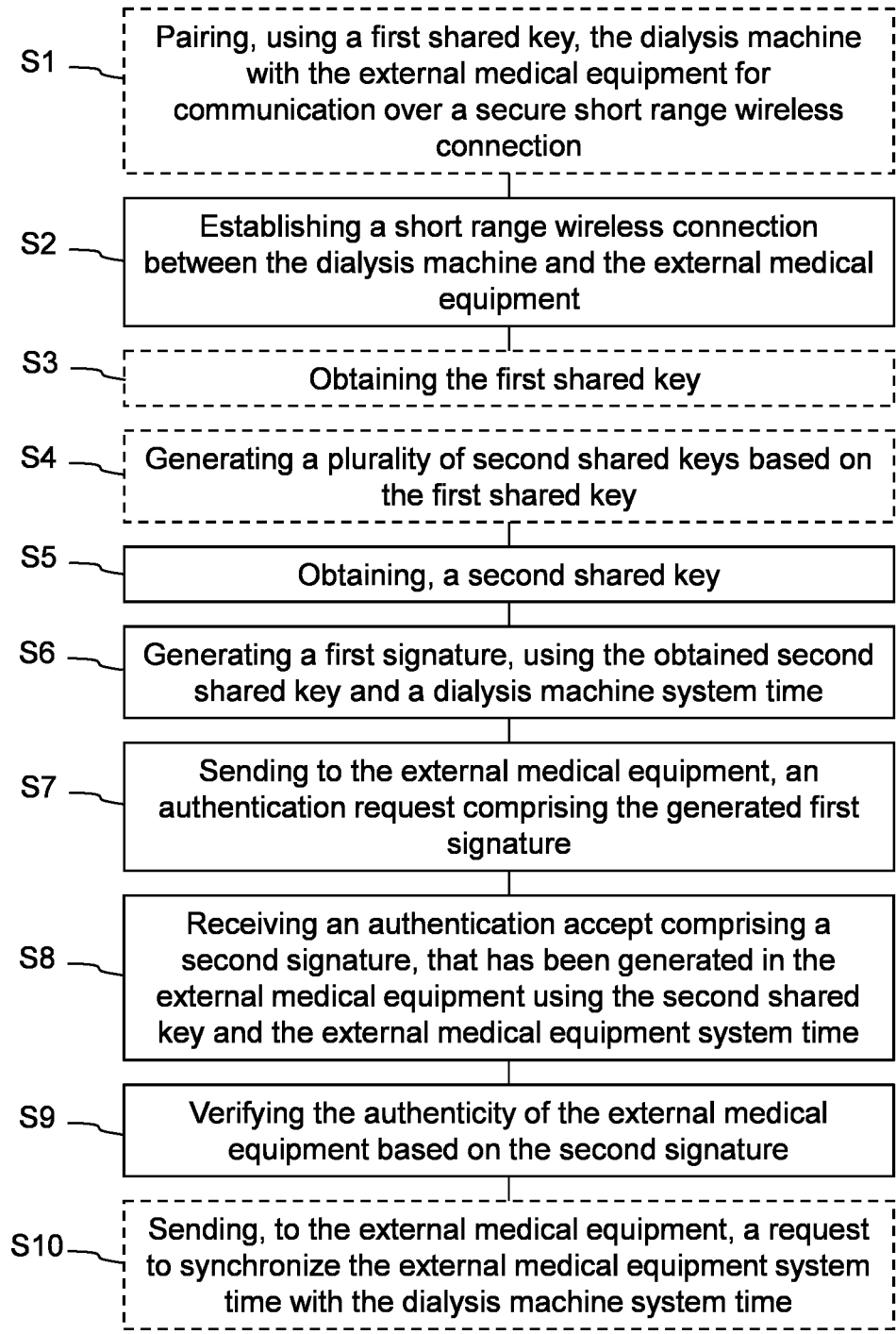
FIG. 2a illustrates a flow chart of a method for use in a dialysis machine.
Figure 2B:
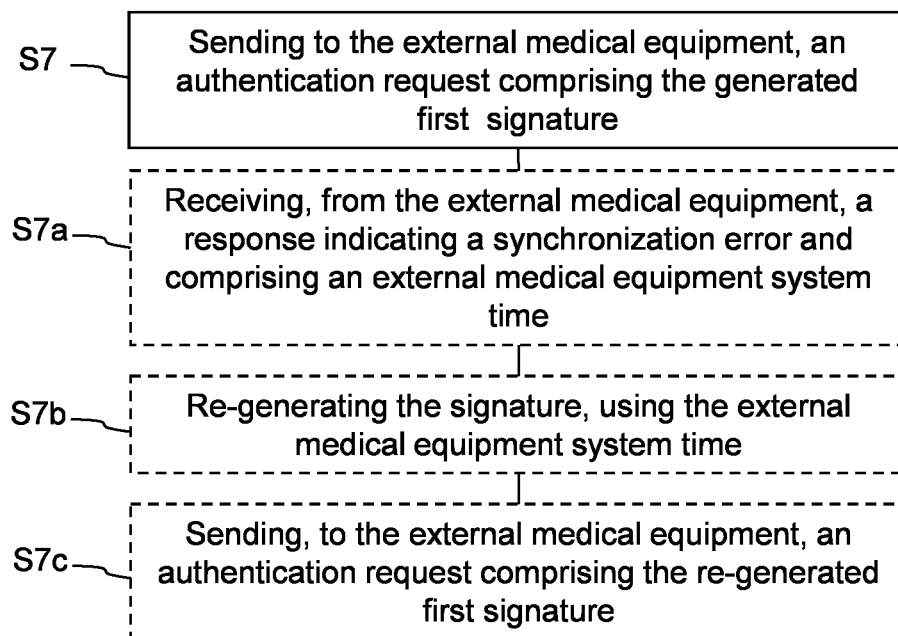
FIG. 2b illustrates some methods steps of the method of FIG. 2a in more detail.

The proposed method, for use in a dialysis machine will now be explained with reference to the flow chart illustrated in FIGS. 2a and 2b and to the illustrations in the other figures. The method is for use in a dialysis machine such as the cycler 20 described above, or any other dialysis machine such as a hemodialysis machine or CRRT machine. That the method is for use in a dialysis machine means that the method steps of the method are performed by one or several components in the dialysis machine. The method may be implemented as program code and saved in a memory unit of the dialysis machine. The steps of the method may be defined in a computer program, comprising instructions which, when the program is executed by a computer e.g. the control unit 22, cause the computer to carry out the method. The steps of the method may also be defined in a computer-readable medium, e.g. a removable memory such as a USB memory stick. The computer-readable medium then comprises instructions, which, when executed by a computer, cause the computer to carry out the method.

The proposed method will be described with reference to the cycler 20 establishing a trusted connection with the water purifier 110 of FIG. 1. However, it must be appreciated that the same method may be used for any medical equipment for use with a cycler 20, such as a scale, a temperature sensor, a fever thermometer, a blood pressure device etc. The method may also be used for connection with external device that is connected to a dialysis machine for other purposes, such as for downloading firmware or similar. Furthermore, the dialysis machine may as well be another type of dialysis machine, such as a hemodialysis machine or a CRRT machine.

For simplicity, the dialysis machine and the external medical equipment will herein sometimes be referred to as simply the "devices". Common for those devices is that it is important for the dialysis machine to verify the authenticity of the external medical equipment before the device is put into use.

The method may be performed at any time when the dialysis machine, such as the cycler 20, is switched on and needs to communicate with external medical equipment, such as the water purifier 110 in FIG. 1. If the dialysis machine is communicating with further external medical equipment, then the method may be performed for each and every of those devices. In a typical scenario, the method steps are performed, when the dialysis machine is switched on.

In order to perform the proposed method a short-range wireless connection first needs to be establish between the external medical equipment and the dialysis machine. Examples of short-range wireless communication protocols that may be used for the short-range wireless connection are Bluetooth™, WiFi™, Zigbee®, Z-Wave®, wireless Universal Serial Bus, USB, or infrared protocols, or via any other suitable wireless communication technology. However, the technique will now be described using the Bluetooth™ standard as an example.

If it is the first time that the dialysis machine communicates with the external medical equipment, then the devices first needs to be paired or bonded. During pairing, the two devices establish a relationship by creating a shared secret known as a link key. If both devices agree on and store the same link key, they are said to be paired or bonded.

There are different pairing mechanisms defined in the Bluetooth™ standards. One example is secure simple pairing using Pass key entry. This method may be used between a device with a simple display, such as the water purifier 110, and a device with numeric keypad entry (such as a keyboard), such as the cycler 20. Then the display presents a 6-digit numeric code to the user, who then enters the code on the keypad.

Other examples of shared keys used for the short-range connection are a Wired Equivalent Privacy, WEP, key used in Wi-Fi or any other PIN code used in connection with the initiation of the short-range wireless connection.

In other words, according to some embodiments the method comprises an initial step of pairing S1 the dialysis machine with the external medical equipment for communication over a secure short-range wireless connection using the first shared key. When this step has been performed, the devices are paired.

Alternatively, if the devices have previously been communicating, i.e. they are already paired or bonded, then an already existing bonding table may be used for establishing the connection. Hence, according to some embodiments this step is optional, which is illustrated with dashed lines in FIG. 2*a*. However, even if the devices have been previously paired the first key may be deleted from either device, which removes the bond between the devices. If one of the devices have deleted the link key, then the pairing needs to be repeated.

Once the two devices have a valid bond, i.e. they are paired, then a short-range connection between the devices may be established. Thus, the proposed method comprises establishing S2 a short-range wireless connection between the dialysis machine and the external medical equipment.

Thus, a Bluetooth™ pass key or link key, herein referred to as the first shared key, is associated with the short-range wireless connection in the sense that it is used to pair the devices. That the first key is shared herein means that it is known by both devices. However, note that the connection as such does typically not require that the devices are in time synchronization. In other words, a system clock of the dialysis machine may typically have a different time than a system clock of the external medical equipment.

The proposed method adds an enhanced authentication procedure on top of the wireless short-range protocol. The added authentication procedure re-utilizes the first shared key to generate a second shared key. This is accomplished by obtaining S3, the first shared key and generating S4 a set of second shared keys based on the first shared key and at least one predetermined criterion that is known by the dialysis machine and the external medical equipment. The Bluetooth™ passkey may be stored in a memory or other data storage (with limited access) in the respective device. The obtaining S3 e.g. corresponds to that the first shared key is read from a memory in the dialysis machine. Alternatively, the generation S4 of the set of second shared keys is performed when the passkey is entered. Then the obtaining S3 corresponds to obtaining the passkey from a user interface. Note that the obtaining S3 and the generating S4 is according to some embodiments performed before the short-range connection is established S2.

The set of second shared keys is e.g. generated by creation of a key table using at least one predetermined criterion, such as an algorithm and one or more cryptographic salts that represent the unique organization and/or product line identifier used by the device manufacturer. In cryptography, a salt is random data that is used as an additional input to an algorithm. The set of second shared keys is unique for every first shared key, which implies that a device needs to have access to both the first shared key and the at least one predetermined criterion or rule to re-create it.

The generated set of second shared keys may be stored e.g. in a memory, for later use. Each second shared key is typically longer than the first shared key. For example, in order to guarantee a certain level of protection the second shared keys may be between 16-256 bits. The number of second shared key may vary depending on circumstances.

The higher the number of second shared keys, the higher security. In a particular case, the set of shared keys comprises only one shared key.

The idea is that the dialysis machine and the external medical equipment both know the at least one predetermined criterion that is used to generate the set of second shared keys. The at least one predetermined criterion is e.g. an algorithm or other formula and possibly some parameters, salts, strings etc. The at least one predetermined criterion is e.g. applied to the first shared key. For example, the algorithm takes the first shared key as an input parameter. In this way two corresponding sets of second shared keys may be generated without any additional key exchange, apart from what is already required to establish the short-range wireless connection. In this disclosure, the set of second shared keys in the dialysis machine is referred to as the "set of second shared keys" and the set of shared keys in the external medical equipment is referred to as the "corresponding set of second shared keys". Typically, these sets are equal, but theoretically it could work if one of the sets is a subset of the other, provided that a second shared key included in both subsets is used.

The set of second shared keys (and the corresponding set of second shared keys) may comprise one or several second shared keys. For example, the second shared keys are stored in a table, where each entry is defined by an index. If there is only one key in the table, then no index is needed.

The obtaining S3 and the generating S4 needs to be repeated every time the Bluetooth™ bonding table is updated. However, if the dialysis machine and the external medical equipment are already paired and the set of second shared keys have already been generated and stored, then these steps need not be performed. Hence, according to some embodiments these steps are optional, which is illustrated with dashed lines in FIG. 2a.

Once the set of second shared keys are created the authentication may be initiated. The authentication is initiated by the dialysis machine, which acts as a master. The external medical equipment acts as a slave.

Authentication is initiated by the dialysis machine selecting one particular second shared key that is to be used for the authentication. In other words, the method comprises obtaining S5 a second shared key from the set of second shared keys. As already mentioned, the set of second shared keys has been generated, in the dialysis machine, using the first shared key. This step typically means that the second shared key is read from a memory, which typically has restricted access. However, it may also be obtained directly from where it is generated.

According to some embodiments, the obtaining S5 comprises randomly selecting one key from the set of second shared keys. Random selection improves security, as it is unpredictable which second shared key will be used.

Then an authentication request is generated using the selected or obtained second shared key. The authentication request typically comprises information such as at least one of: dialysis machine system time, generation time of the authentication request, expiry time of the authentication request, and a device identity. If the obtained second shared key is randomly selected from a set of shared keys that comprises multiple entries, then the authentication request typically also has to comprise an identifier defining the particular second shared key. The identifier is e.g. an index of a table comprising the set of second shared keys.

Figure 3B:
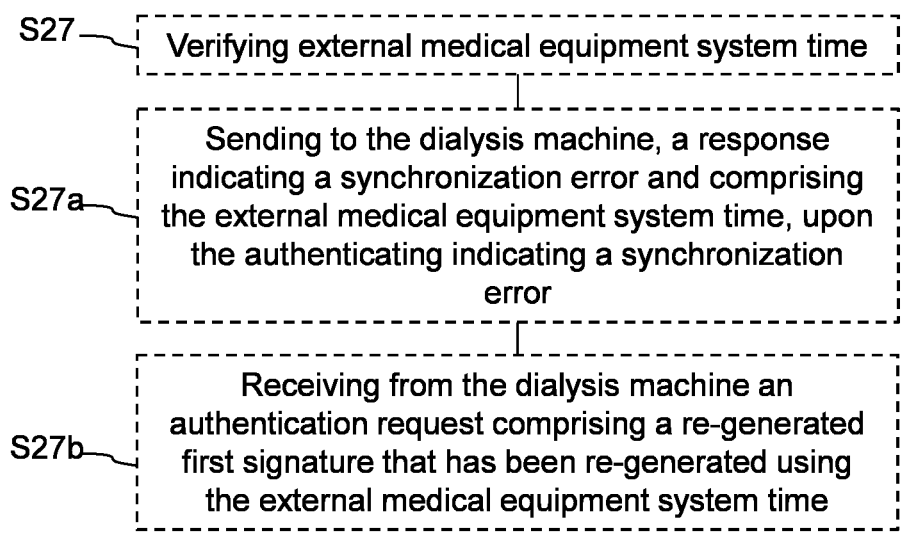
FIG. 3b illustrates some methods steps of the method of FIG. 3a in further detail.
Figure 3A:
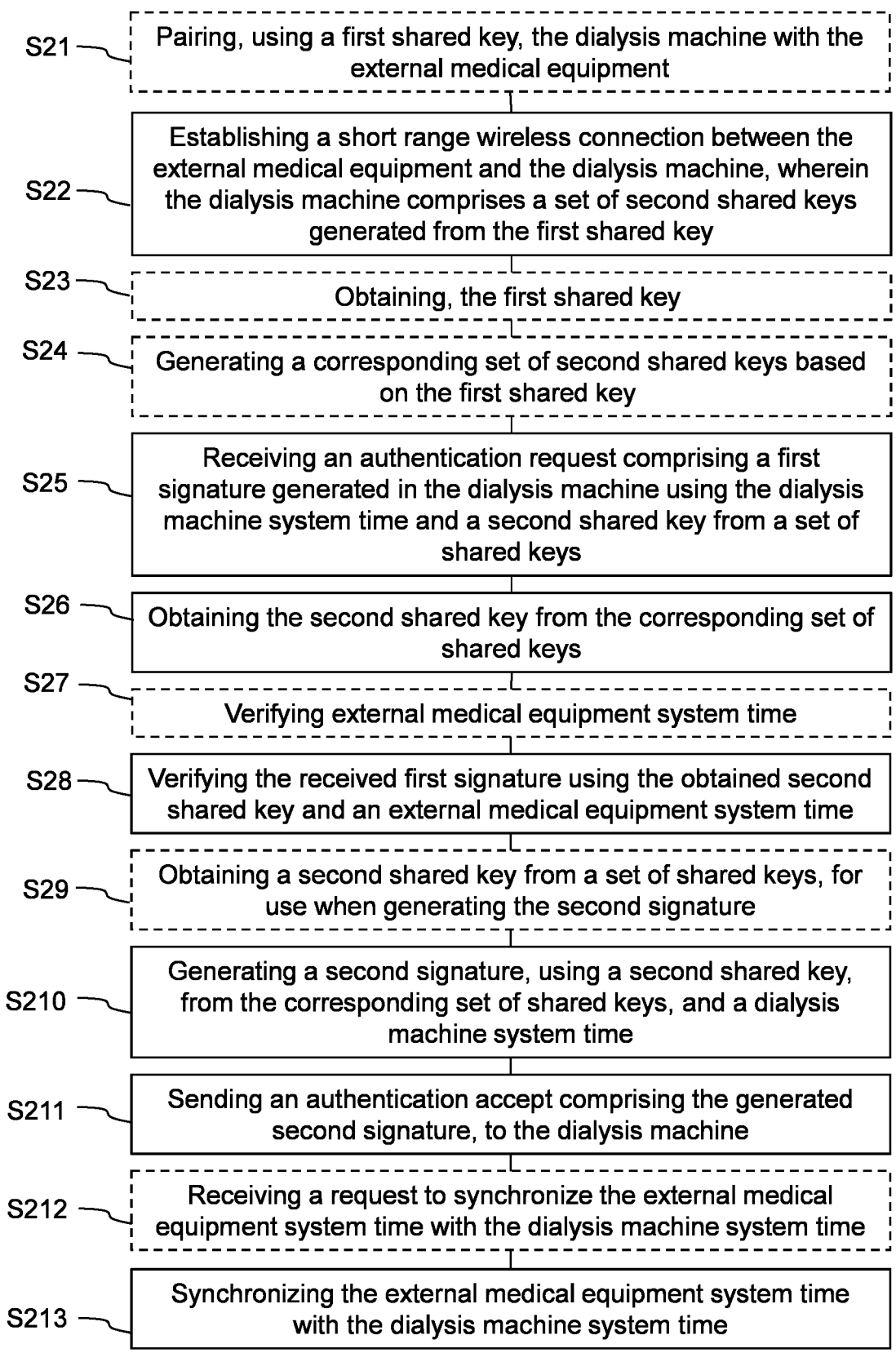
FIG. 3a illustrates a flow chart of a method for use in external medical equipment.

The authentication request also comprises a cryptographic signature, herein referred to as a first signature. The cryptographic signature is e.g. generated taking the first shared key and the other data in the authentication request as input. The first signature may then be appended to the other data in the authentication request. According to some aspects the first signature is generated using a cryptographic hash function. The first signature may be used by a receiving part to verify the authenticity of the authentication request as will be further explained below (FIG. 3a).

In other words, the method comprises generating S6 a first signature, using the obtained second shared key and a dialysis machine system time. In a particular embodiment, the dialysis machine system time is not included in the authentication request and the generating is not based on the dialysis machine system time. The use of at least one predetermined criterion to generate the set of second shared keys ensures that secure short-range communication is only established with trusted devices that knows the at least one predetermined criterion, e.g. devices provided by the manufacturer of the dialysis machine or its partners. The manufacturer of the dialysis machine may then make sure that the dialysis machine is never used with unknown external medical equipment, that may jeopardize safety of the dialysis treatment or cause damage to the dialysis machine, which would be the case if using only e.g. the open Bluetooth™ protocol.

In an example embodiment, the authentication request is implemented using Json Web Token, JWT. JWT is an authentication protocol that is widely used on the internet to authenticate servers and clients. JWT is an open standard (more specifically JSON Web Token (JWT)-RFC 7519) that defines a compact and self-contained way for securely transmitting information between parties as a Json object. This information can be verified and trusted because it is digitally signed. JWTs can be signed using a secret (with the HMAC algorithm) or a public/private key pair using RSA. Furthermore, it is a flexible standard that allows using specific parameters and still signing the authentication request in a standard way. Furthermore, it is easy to implement as there is open source code that may be reused. Hence, the protocol is efficient, easy and thoroughly tested.

When the authentication request is created, it is sent to the external medical equipment. In other words, the method then comprises sending S7 the authentication request comprising the generated first signature to the external medical equipment. The sending typically comprises sending the authentication request e.g. a Json web token, over the short-range wireless connection. The external medical equipment may then authenticate the dialysis machine based on the authentication request. This is e.g. done by re-generating the first signature of the authentication request using the same cryptographic function and second shared key and comparing the result with the received first signature.

If the authentication is successful (i.e. if there is a match between the signatures) the same procedure will be repeated by the external medical equipment. Consequently, the external medical equipment will generate a signed authentication accept (or authentication response) and send it back to the dialysis machine. This message is equal or similar to the authentication request sent by the dialysis machine. The signature of the authentication accept is herein referred to as a second signature. According to some aspects the second signature is generated using a hash function. Typically, the same as when generating the first signature. The creation of the authentication accept will be further described in relation to the method performed in the external medical equipment (FIG. 3a).

The dialysis machine will then receive the authentication accept. In other words, the method for use in the dialysis machine then comprises, receiving S8, from the external medical equipment, an authentication accept comprising a second signature. The second signature has been generated in the external medical equipment using the external medical equipment system time and a second shared key from the corresponding set of second shared keys. As described above, the corresponding set of second shared keys has been generated in the external medical equipment using the first shared key.

The dialysis machine can then verify the authenticity of the external medical equipment through the second signature. Thus, the method for use in the dialysis machine then comprises, verifying S9 the authenticity of the external medical equipment using the second signature. For example, the second signature is re-generated using the same cryptographic function e.g. a hash function. The re-generated second signature is then compared with the received second signature to verify that there is a match. If the verification is successful i.e. if there is a match, then the dialysis machine knows that the external medical equipment is authentic and that it can be trusted. The medical equipment may then go into a service mode, which means that the external medical equipment is typically only connectable (i.e. discoverable) for a short time, until the secure connection has been established. Then the external medical equipment is not discoverable any more. Thus, after the secure connection has been established the external medical equipment may operate in a service mode, where it cannot be accessed by other parties.

As mentioned above, the standard Bluetooth™ pairing does not provide any time synchronization of the paired devices. Hence, in some cases the difference in time between the system clocks of the dialysis machine and the external medical equipment may cause problems in the authentication, even if they are paired. This is an issue that cannot be handled by e.g. the proposed JWT protocol, as web servers are typically synchronized in time.

When using the proposed method this may be solved as follows, see detailed flow chart of FIG. 2b. If the medical equipment encounters a time synchronization error, i.e. that the time difference between the system time of the dialysis machine and the external medical equipment is above a predefined level, then the external medical equipment responds with a response indicating a synchronization error. The response will include the system time of the external medical equipment. Reception of such a response will cause the dialysis machine to repeat the procedure of generating the authentication request, but using the system time of the external medical equipment instead. As the first signature is dependent on the system time, the first signature also needs to be re-generated. This may be done using the same second shared key as in the original attempt, or a new second shared key may be obtained.

In other words, according to some embodiments the method comprises, upon receiving S7a from the external medical equipment a response indicating a synchronization error and comprising external medical equipment system time, re-generating S7b the first signature, using the external medical equipment system time. The method then comprises sending S7c, an authentication request comprising the re-generated first signature to the external medical equipment. The external medical equipment is then typically able to verify the (re-generated) authentication request, as it has been generated the external medical equipment's own system time. Thus, there cannot be a synchronization error. Consequently, the external medical equipment may proceed and generate and send the authentication accept as described above.

The dialysis machine is in this case also aware of the time synchronization problem. Hence, it may also consider the problem when receiving the authentication accept. Thus, the dialysis machine may select to use the external medical equipment system time when verifying the verification accept. If this is not done, the same synchronization problem as described above may occur in the dialysis machine. Hence, according to some embodiments, the verifying S9 comprises verifying the authenticated connection using the external medical equipment system time.

When the second signature has been verified in the dialysis machine, a trusted relation has been established between the dialysis machine and the external medical equipment. Then, it is typically desirable to update the system clocks of the devices, to avoid future synchronization errors. Hence, according to some embodiments the method comprises sending S10, to the external medical equipment, a request to synchronize the external medical equipment system time with the dialysis machine system time.

A corresponding method for establishing an authenticated connection between external medical equipment and a dialysis machine performed in the external medical equipment will now be described referring to FIGS. 3a and 3b. The method is typically performed in the external medical equipment in parallel (or at least partly in parallel) with the method for use in the dialysis machine described in FIGS. 2a and 2b. The method is for use in external medical equipment, such as the water purifier 110 of FIG. 1, described above. The method may be implemented as program code and saved in a memory of the external medical equipment. Thus, the steps of the method may be defined in a computer program, comprising instructions which, when the program is executed by a computer e.g. the control unit 22 (FIG. 1), cause the computer to carry out the method. Thus, the steps of the method may also be defined in a computer-readable medium, e.g. a removable memory such as a USB memory stick. The computer-readable medium then comprises instructions, which, when executed by a computer, cause the computer to carry out the method.

As described above, the dialysis machine and the external wireless device need to be paired before any short-range connection can be established. This needs to be done if there is no valid bond between the devices, e.g. if no bonding table has been created or if the bonding table has been deleted. Hence, according to some aspects, the method comprises an initial step of pairing S21 the dialysis machine with the external medical equipment for communication over a secure short-range wireless connection. As explained above, the pairing uses a first shared key, such as a passkey or link key. This corresponds to step S1 in the method of FIG. 3a.

The method then comprises establishing S22 a short-range wireless connection between the external medical equipment and the dialysis machine. This step corresponds to step S2 in the method of FIG. 3a. As described above, a first shared key is associated with the short-range wireless connection. Furthermore, as described above in connection with FIG. 2a, the dialysis machine comprises a set of second shared keys generated in the dialysis machine from the first shared key.

As explained above, the authentication is based on using a second shared key from a set of shared keys. As explained above, the dialysis machine and the external medical equipment generate corresponding sets of second shared keys using at least one predetermined rule or criterion and a first shared key. This step does not need to be performed for every authentication. However, in some scenarios the corresponding set of second shared keys needs to be re-generated. This may be the case e.g. after a pairing or if the set of second shared keys has been deleted. In other words, according to some embodiments the method comprises obtaining S23, the first shared key and generating S24 a set of second shared keys based on the first shared key. Note that the obtaining S23 and the generating S24 is according to some embodiments performed before the wireless short-range connection is established S22.

The actual authentication procedure, is typically started by the dialysis machine. Thus, in the external medical equipment, the authentication procedure is initiated upon receiving an authentication request from the dialysis machine. In other words, the method for use in the external medical equipment comprises receiving S25 from the dialysis machine, an authentication request comprising a first signature, wherein the first signature has been generated in the dialysis machine using the dialysis machine system time and a second shared key from a set of second shared keys. This step corresponds to receiving the authentication request generated in step S7 above.

The method then comprises obtaining S26 the second shared key from a corresponding set of second shared keys that has been generated in the external medical equipment from the first shared key. In other words, the external medical equipment needs to find the particular key that has been used to generate the received authentication request. This is e.g. done based on information comprised in the authentication request. For example, the authentication request comprises an index that is used to read an entry in a table, where the set of second shared keys are stored. Stated differently, according to some embodiments, the second shared key is obtained from the table using an index of the table comprised in the authentication request. If the set of shared keys only comprises one shared key, then that key is simply used.

The authentication request is then verified. The verification may comprise that data comprised in the request, e.g. the first signature, is checked or verified. As mentioned above this may be done by re-generating the first signature using the same cryptographic algorithm as used when generating the signature. The cryptographic algorithm may be defined by the protocol used. In other words, the method typically comprises at least verifying S28 the authenticity of the dialysis machine using the obtained second shared key and external medical equipment system time. The verifying S28 may also comprise verifying other data comprised in the authentication request such as dialysis machine identity (e.g. a device ID), creation time of the first signature, i.e. that the validity of the first signature has not expired.

If the authentication request can be verified, which is the case if the first signature is valid, then an authentication accept is sent in response to the request. As mentioned above, the verification S28 may according to some embodiments also take into account other data comprised in the request, such as system time information, expiry time, dialysis machine identity information etc. The authentication accept (or response) sent in response to the authentication request typically comprises a signature generated in the external medical equipment, herein referred to as a second signature. In the same way as the first signature, the second signature is generated using a second shared key. Hence, in the same way as when generating the first signature, a second shared key from the corresponding set of shared keys is obtained, e.g. by randomly selecting one second shared key from a table. Stated differently, according to some embodiments, the method comprises obtaining S29 a second shared key from a set of second shared keys, for use when generating the second signature.

In other words, the method for use in the external medical equipment comprises generating S210, upon the verifying S28 being successful, a second signature, using a second shared key, from the corresponding set of second shared keys, and a dialysis machine system time. The method further comprises sending S211 an authentication accept comprising the generated second signature, to the dialysis machine. The authentication accept typically has the same, or a similar, format as the authentication request e.g. JWT. The authentication is then received and verified by the dialysis machine as described in step S8 and step S9 above. Thus, the second signature may be used by the dialysis machine to verify that the external medical equipment is authentic or trusted. After successful verification of the second shared key in the dialysis machine, then the authentication is completed. For example, the water purifier 110 is considered to be an authentic water purifier.

As explained above, the dialysis machine may, after successful authentication, request S1l the external medical equipment to update its system time to match the system time of the dialysis machine. In other words, according to some embodiments the method comprises receiving S212 from the dialysis machine a request to synchronize the external medical equipment system time with the dialysis machine system time. This step corresponds to the request to synchronize the external medical equipment system time of step S10 described in connection with FIG. 3a.

As discussed above, the system time of the dialysis machine and the external medical equipment are not necessarily in synchronization, which may cause problem in the authentication. In order to mitigate problems related thereto, the external medical equipment may compare the dialysis machine system time received in the authentication request with an internal external medical equipment system time. In other words, according to some embodiments the method comprises verifying S27 the external medical equipment system time. If the verification indicates a time difference (or time shift) between the system clock of the dialysis machine and the medical equipment system time that is above a threshold, then the authentication request is not accepted, and instead some kind of error message is returned to the dialysis machine. The threshold may be predefined or it may be manually updated based on e.g. trial data. In other words, the method comprises, upon the verifying indicating that the dialysis machine system time and the external medical equipment system time differing above a pre-determined amount sending S27a to the dialysis machine, a response indicating a synchronization error and comprising the external medical equipment system time. As explained above in connection with (FIG. 3b), the dialysis machine will receive S7a the response indicating a synchronization error, and respond to the response indicating a synchronization error by re-generating S7b using the external medical equipment system time and re-sending S7c the authentication request.

Consequently, the method for use in the external medical equipment according to some embodiments comprises receiving S27b from the dialysis machine an authentication request comprising a re-generated first signature that has been re-generated using the external medical equipment system time.

Figure 4A:
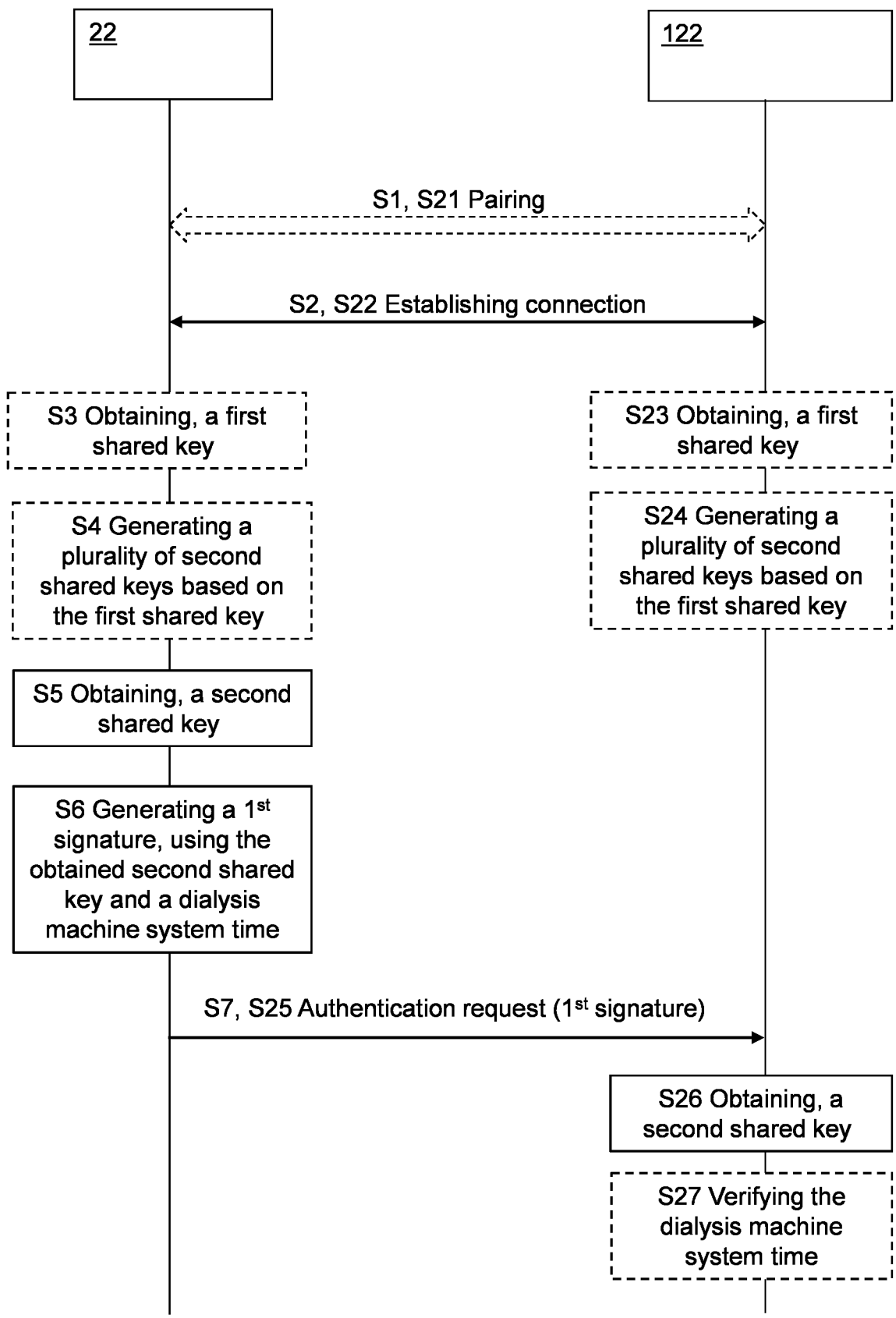
FIGS. 4a and 4b illustrate signaling between the dialysis machine and the external medical equipment, when performing the methods of FIGS. 2a-2b and FIGS. 3a-3b.
Figure 4B:
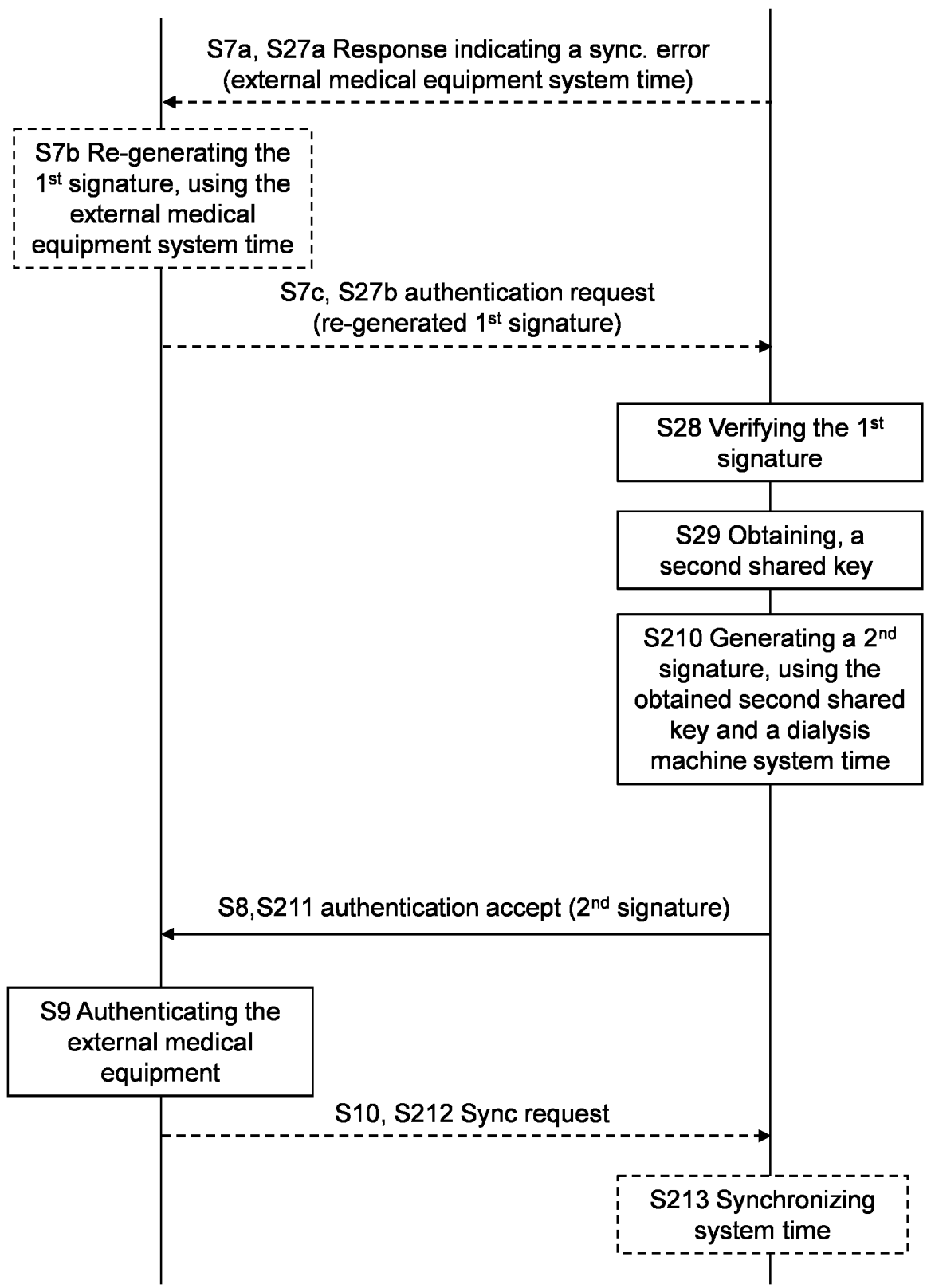

FIGS. 4a and 4b is a signaling diagram illustrating signaling between the dialysis machine and the external medical equipment, when performing the methods of FIGS. 2a-2b and FIGS. 3a-3b. FIGS. 4a and 4b the interaction between dialysis machine and the external medical equipment performing the respective methods can be seen.

Figure 5:
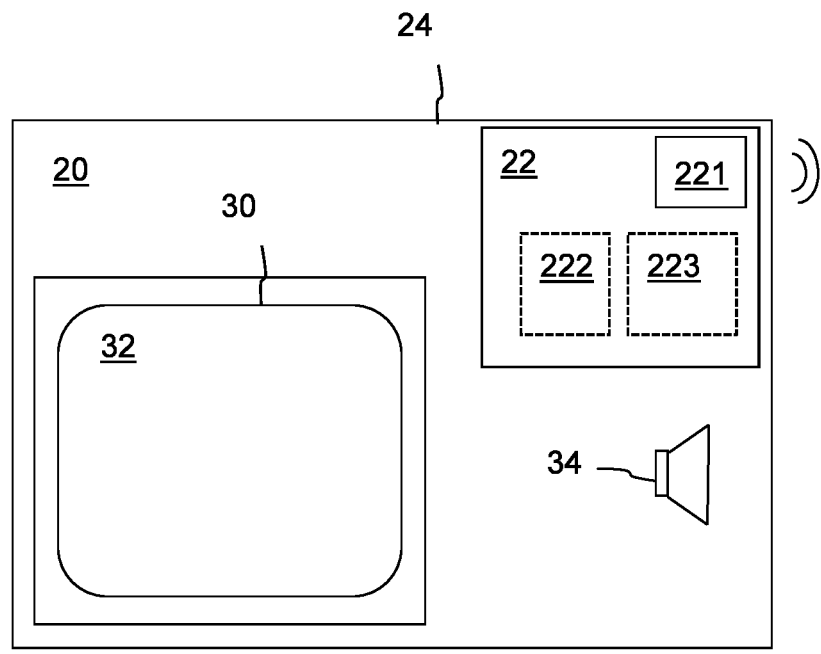
FIG. 5 illustrates a dialysis machine according to some example embodiments.

An example implementation of a dialysis machine configured to perform the methods described above will now be described using the cycler 20 of FIG. 1 as an example. Reference is in particular made to FIG. 5 illustrating the cycler 20 in more detail. Note that FIG. 5 is only a conceptual drawing and that it mainly illustrates parts of the cycler 20 that are related to the proposed technique.

The cycler 20 comprises a housing 24, a user interface 30, a speaker 34 and a control unit 22 also referred to as control circuitry.

The control unit 22 typically comprises one or more microprocessors 222 and/or one or more circuits, such as an application specific integrated circuit (ASIC), field-programmable gate arrays (FPGAs), and the like.

The control unit 22 comprises short-range communication interface 221. The short-range communication interface 221 comprises a wireless communication circuit configured for sending information to and receiving information from control unit 22 of external medical equipment, herein exemplified by the water purifier 110 of FIG. 1. Wireless communication may be performed via any of Bluetooth™, WiFi™, Zigbee®, Z-Wave®, wireless Universal Serial Bus ("USB"), or infrared protocols, or via any other suitable wireless communication technology. The short-range communication interface 221 is for example a Bluetooth™ chip, configured to be controlled by the one or more microprocessors 222, e.g. through AT commands. The short-range communication interface 221 is according to some embodiments arranged external to the control unit 22.

According to some embodiments the control unit 22 comprises at least one memory 223, such as a non-transitory memory unit (e.g., a hard drive, flash memory, optical disk, etc.) and/or volatile storage apparatuses (e.g., dynamic random access memory (DRAM)). The memory 223 is configured to store data such as the first and the second shared keys or a computer program configured to execute the proposed method.

The user interface 30 e.g. includes a display 32, which may operate with a touch screen overlay placed onto the display 32 for inputting commands via user interface 30 into control unit 22. The user interface 30 may also include one or more electromechanical input device, such as a membrane switch or other button, e.g. a key board (not shown). The user interface is e.g. configured to display a Bluetooth™ passkey to a user or to let a user input a Bluetooth™ passkey. The control unit 22 may further include an audio controller for playing sound files, such as voice activation commands, at the speaker 34. The speaker may e.g. indicate to a user when the cycler 20 is paired.

The control unit 22 is configured to cause the cycler 20 to perform all aspects of the method described above (FIG. 2a-c). For example, the one or more microprocessors 222 are configured to execute a computer program stored in the memory 223 to achieve this. Thus, the method referred to herein is implemented as a program.

In more particular, the control unit 22 is configured to cause the cycler 20 to establish, using the short-range communication interface 221, a short-range wireless connection between the cycler 20 and a water purifier 110, wherein a first shared key is associated with the short-range wireless connection. The control unit is further configured to obtain a second shared key from a set of second shared keys, wherein the set of second shared keys has been generated, in the cycler 20, using the first shared key and to generate a first signature, using the obtained second shared key and a cycler system time. Furthermore, the cycler is configured to send, using the short-range communication interface 221, to the water purifier 110, an authentication request comprising the generated first signature and to receive, using the short-range communication interface 221, from the water purifier 110, an authentication accept comprising a second signature. The second signature has been generated in the water purifier 110 using a water purifier system time and a second shared key from a corresponding set of second shared keys. As already explained above, the corresponding set of second shared keys has been generated in the water purifier 110 using the first shared key. Finally, the cycler is configured to verify the authenticity of the water purifier 110 based on the second signature. In other words, the control unit 22 is configured to establish a secure communication with the water purifier 110 as described above (FIG. 2a).

According to some embodiments the control unit 22 is configured to cause the cycler 20 to, upon receiving, from the water purifier, a response indicating a synchronization error and comprising a water purifier system time re-generate the first signature, using the water purifier system time and send, using the short-range communication interface, an authentication request comprising the re-generated first signature to the water purifier. Then the control unit is typically also configured to verify the authenticated connection using the water purifier system time and the re-generated signature. In other words, the control unit 22 is configured to use the water purifier system time during the authentication procedure, in response to receiving a message that indicates that there is a synchronization error.

According to some embodiments the control unit 22 is configured to cause the cycler 20 to pair the cycler with the water purifier for communication over a secure short-range wireless connection, using the first shared key.

According to some embodiments the control unit 22 is configured to cause the cycler 20 to obtain the second shared key by randomly selecting one key from the set of second shared keys.

According to some embodiments the control unit 22 is configured to cause the cycler 20 to obtain the first shared key and to generate a set of second shared keys based on the first shared key and at least one predetermined criterion that is known by the cycler 20 and the water purifier 110.

According to some embodiments the control unit 22 is configured to cause the cycler 20 to send, using the short-range communication interface 221, a request to synchronize the water purifier system time with the cycler system time to the water purifier.

According to some embodiments the control unit 22 is configured to generate a request comprising at least one of an expiry time, a present time, a device name.

Figure 6:
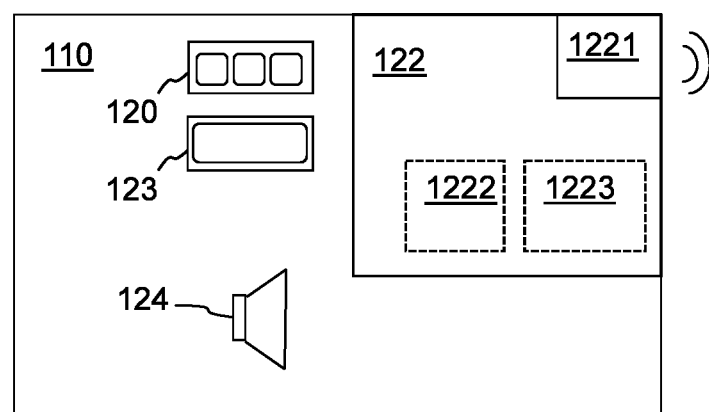
FIG. 6 illustrates a control unit of external medical equipment according to some example embodiments.

An example implementation of external medical equipment configured to perform the methods described above, will now be described using the water purifier 110 of FIG. 1 as an example. Reference is in particular made to FIG. 6 illustrating the water purifier 110 in more detail. Note that FIG. 6 mainly illustrates parts of the water purifier 110 that are related to the proposed technique.

The water purifier 110 comprises a control unit 112, also referred to as control circuitry, a user interface 120 and a speaker 124.

The control unit 112 typically comprises one or more microprocessors 1122 and/or one or more circuits, such as an application specific integrated circuit (ASIC), field-programmable gate arrays (FPGAs), and the like.

According to some embodiments the control unit 112 comprises short-range communication interface 1121. The short-range communication interface 1121 comprises a wireless communication circuit configured for sending information to and receiving information from control unit 22 of cycler 20. In the example of FIG. 6 the short-range communication interface 121 is comprised in the control unit 112. Wireless communication may be performed via any of Bluetooth™, WiFi™, Zigbee®, Z-Wave®, wireless Universal Serial Bus ("USB"), or infrared protocols, or via any other suitable wireless communication technology. The short-range communication interface 1121 is for example a Bluetooth™ chip, configured to be controlled by the included one or more microprocessors 1122, e.g. through AT commands. According to some embodiments the short-range communication interface 1121 is arranged external to the control unit 112.

According to some embodiments the control unit 112 comprises at least one memory 1123, such as a non-transitory memory unit (e.g., a hard drive, flash memory, optical disk, etc.) and/or volatile storage apparatuses (e.g., dynamic random access memory (DRAM)). The memory 1123 is configured to store data such as the first and the second shared keys or a computer program configured to execute the proposed method.

The user interface 120 comprises a display 123 and one or more electromechanical input device, such as a membrane switch or other button. However, the user interface 120 does typically not comprise a proper keypad suitable for passkey entry. The display 123 is configured receive data from the control unit 112 to show the data (e.g. a Bluetooth™ passkey) to a user. The control unit 112 may further comprise an audio controller for playing sound files, such as alarm or alert sounds, at one or more speaker 124 of water purifier 110.

The control unit 112 is configured to cause the water purifier 110 to perform all aspects of the method described above (FIG. 3*a*-*c*). For example, the one or more microprocessors 1122 are configured to execute a computer program stored in the memory 1123 to achieve this.

In more particular, the control unit 112 is configured to cause the water purifier 110 to receive, using the short-range communication interface 1221, from the water purifier 110, an authentication request comprising a first signature. As explained above, the first signature has been generated in the cycler 20 using the cycler system time and a second shared key from a set of second shared keys. Furthermore, the water purifier is configured to obtain the second shared key from a corresponding set of second shared keys that has been generated in the external medical equipment from the first shared key and to verify the authenticity of the cycler using the obtained second shared key and external medical equipment system time and to generate, upon successful verification of the authenticity of the cycler, a second signature, using a second shared key, from the corresponding set of second shared keys, and a cycler system time. Finally, the water purifier is configured to send, using the short-range communication interface 1221, an authentication accept comprising the generated second signature, to the cycler 20.

According to some embodiments the control unit 112 is configured to cause the water purifier 110 to compare the external medical equipment system time and the cycler system time, and to send, using the short-range communication interface 1221, a response indicating a synchronization error and comprising the water purifier system time upon the cycler system time and the external medical equipment system time differing above a pre-determined amount. Then the water purifier is configured to receive, from the cycler 20, an authentication request comprising a re-generated first signature that has been re-generated using the water purifier system time, using the short-range communication interface 1221.

According to some embodiments the control unit 112 is configured to cause the water purifier 110 to pair the cycler 20 with the water purifier 110 for communication over a secure short-range wireless connection, using the first shared key.

According to some embodiments the control unit 122 is configured to cause the water purifier 110 to obtain, the first shared key and generate a set of second shared keys based on the first shared key.

According to some embodiments the set of second shared keys comprises a table of shared keys and wherein the second shared key. Then the control unit 122 is configured to cause the water purifier 110 to obtain the second shared key, from the table, using an index of the table comprised in the authentication request.

According to some embodiments the control unit 122 is configured to cause the water purifier 110 to obtain a second shared key from a set of second shared keys, for use when generating the second signature.

According to some embodiments the control unit 122 is configured to cause the water purifier 110 to receive from the cycler 20, using the short-range communication interface 1221, a request to synchronize the water purifier system time with the cycler system time.

FIGS. 7*a*-7*d* illustrates signaling between the cycler 20 and the water purifier 110 (typically between the control unit 22 of the cycler 20 and the control unit 122 in the water purifier 110) according to an example implementation of the methods described in FIG. 2*a*-*b* and FIG. 3*a*-*b*.

Figure 7A:
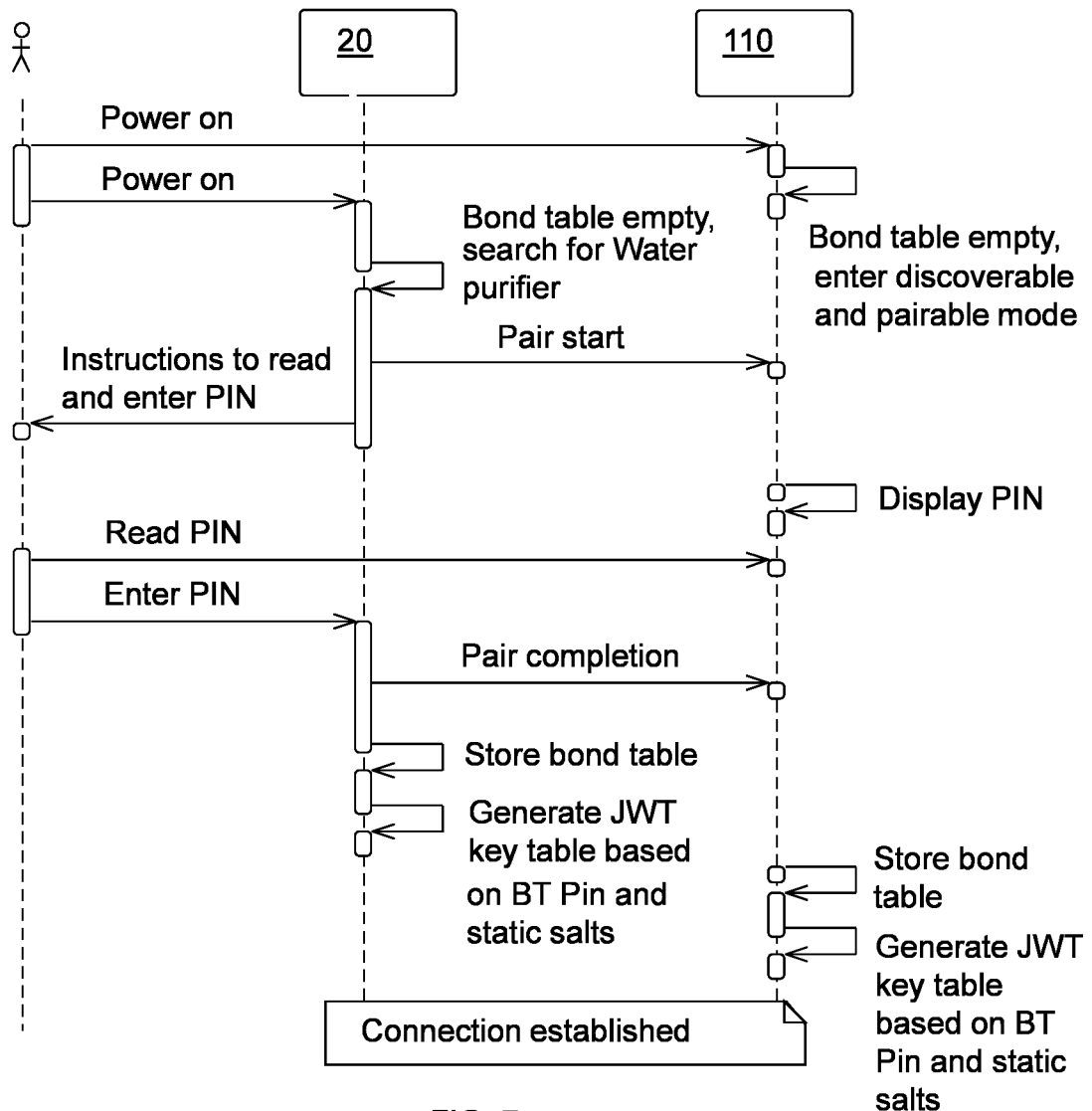
FIGS. 7a-7f illustrate signaling according to an example implementation of the proposed methods.

FIG. 7*a* illustrates signaling during a first Bluetooth™, BT, connect, i.e. a BT pairing. This corresponds to steps S1-S4, S21-S24 in the methods above.

In FIG. 7*a* a patient installer who wants to connect a new cycler 20 powers on the cycler 20 and a water purifier 110. Thus, the cycler 20 has no bond table or a previously cleared bond table. The water purifier 110 does also not have any bond table.

The water purifier 110 then needs to be discoverable. A standard BT pairing is started by the cycler being the master. A pass key is displayed to the user on the display 123. The user inputs the pass key on the keypad of the cycler 20. The pairing procedure may then be completed by the wireless communication interface 221 of the cycler 20 and the wireless communication interface of the water purifier 1121 and bond tables are stored in the respective devices.

The cycler and the water purifier generates a respective JWT key table, including keys to be used for further authentication. The Bluetooth™, BT, connection has now been established.

Figure 7B:
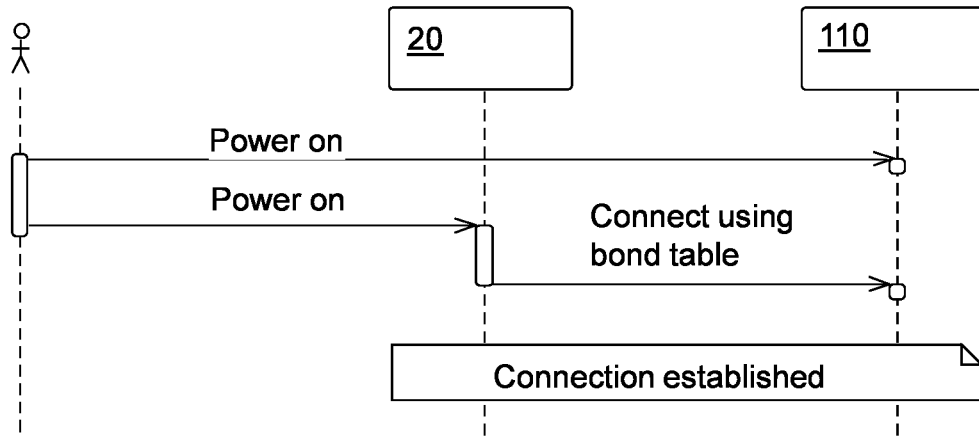

FIG. 7*b* illustrates signaling during a BT connection between already paired devices, i.e. a cycler 20 with bond table and a water purifier 110 with bond table. This corresponds to steps S2, S22 in the methods above. In this scenario, there are already valid bond tables. Hence, after power on a BT connection may be established at power on without any other action being taken.

Figure 7C:
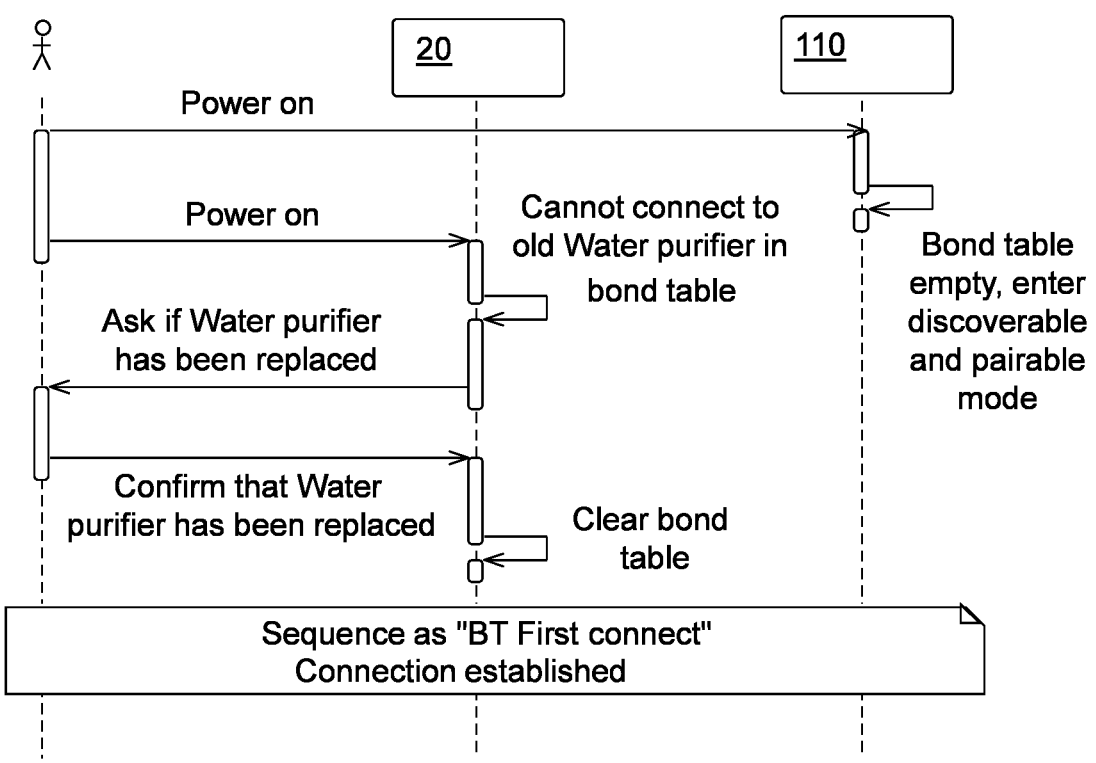

FIG. 7*c* illustrates signaling during a BT connection to new water purifier being established. This corresponds to steps S1-S4, SS-S4 in the methods above.

In this example, a patient/installer has a new water purifier that has no bond table and a cycler 20 with bond table of an old water purifier. When attempting to establish the BT connection the cycler 20 will detect that the bond tables do not match. Hence, the cycler will ask the user/installer if the water purifier 110 has been replaced. Upon the use/installer confirming this the cycler will delete its bond table and perform the same procedure of first BT connection illustrated in FIG. 7a.

Figure 7D:
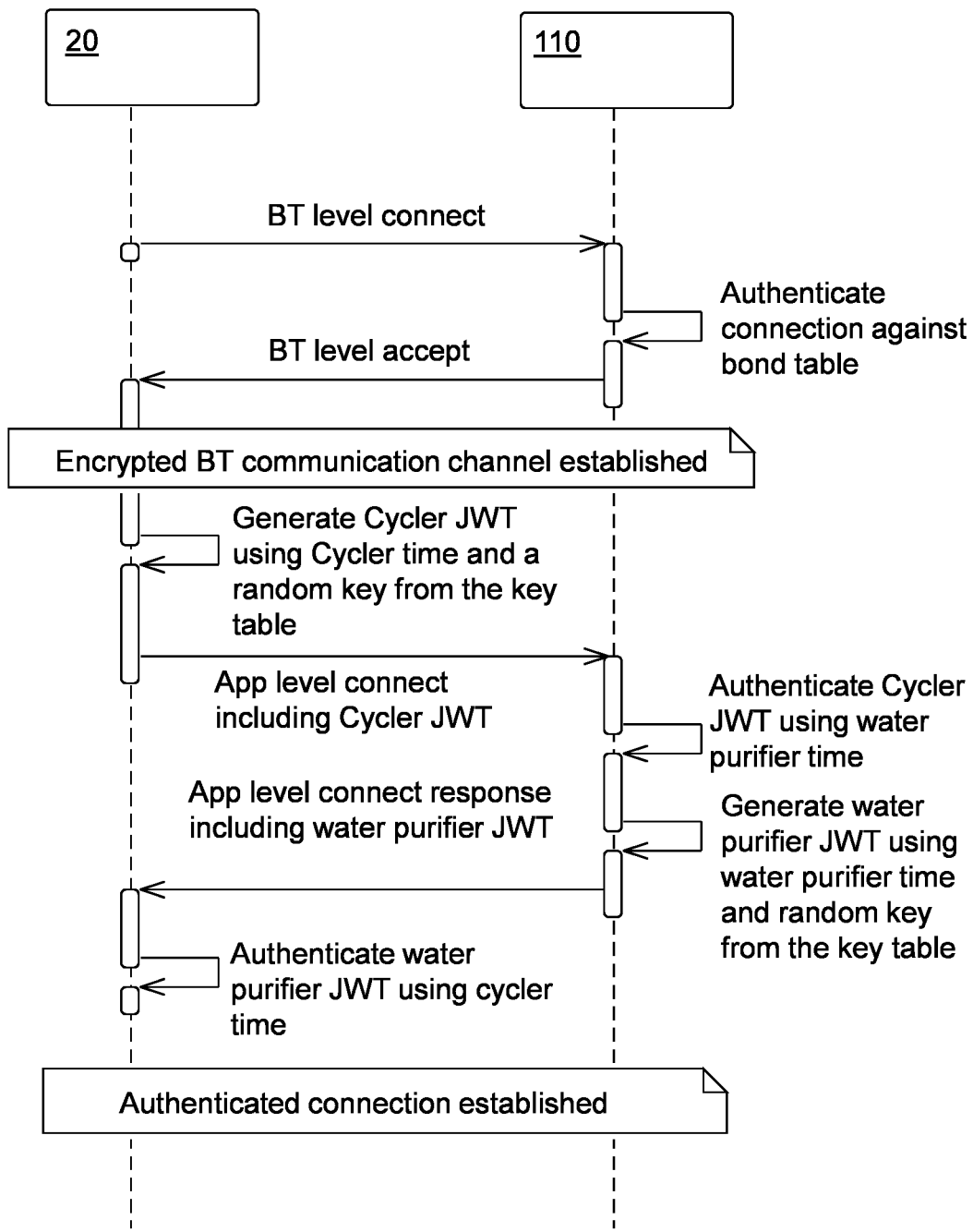

FIG. 7d illustrates signaling during a BT Connection authentication using the enhanced authentication proposed herein. This corresponds to steps S5-10, S25-S213 in the methods above. Hence these steps are performed after any of the sequences of FIG. 7a to 7c.

Thus, the signaling is performed between a cycler 20 with bond table and JWT key table and the water purifier 110 with bond table and JWT key table.

Hence, the BT communication may be established through standard signaling for BT connection.

The cycler then initiates the authentication by generating a Cycler JWT using Cycler time and a random key from the key table.

At application level a connect message including the Cycler JWT is transmitted to the water purifier 110. The water purifier 110 authenticates Cycler JWT using Water purifier time and Generate water purifier JWT using Water purifier time and random key from the key table. The water purifier 110 sends an App level connect response including the water purifier JWT to the cycler 20. Then the water purifier authenticates the water purifier JWT using cycler time, whereby authenticated connection established.

Figure 7E:
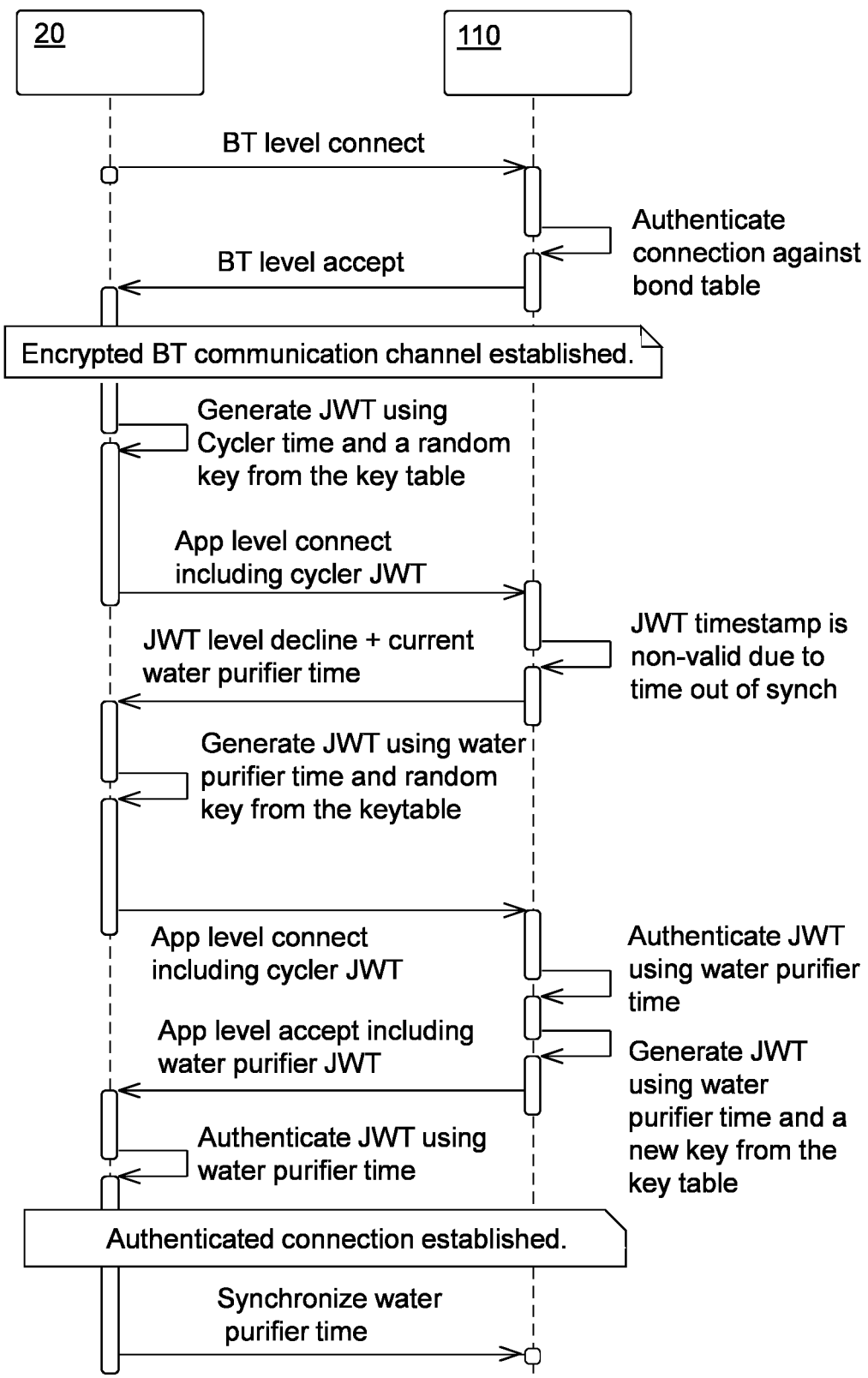

FIG. 7e illustrates signaling during a BT Connection authentication using the enhanced authentication proposed herein, when system time of the cycler 20 and the water purifier 112 are out of synch. This corresponds to steps S5-10, S25-S213 in the methods above. FIG. 7e corresponds to the embodiment of the methods illustrated in FIG. 2b and FIG. 3b.

Thus, the signaling is performed between a cycler 20 with bond table and JWT key table and the water purifier 110 with bond table and JWT key table.

The example embodiment of FIG. 7e differs from the example embodiment of FIG. 7d in that the first JWT timestamp is non-valid due to time out of synch. This causes the water purifier 110 to send a JWT level decline plus a current Water purifier time to the cycler in response to the app level connect message.

The cycler 20 then generate a new JWT using water purifier time and random key from the key table. The cycler then sends a second app level connect including cycler JWT to the water purifier 110.

The water purifier 110 authenticates Cycler JWT using Water purifier time and Generates water purifier JWT using Water purifier time and random key from the key table. The water purifier 110 sends an app level connect response including the water purifier JWT to the cycler 20. Then the water purifier authenticates the water purifier JWT using water purifier time, whereby authenticated connection established. When authentication connection has been established the cycler asks the water purifier to update its system time to match the cycler's system time in order to avoid future errors.

Figure 7F:
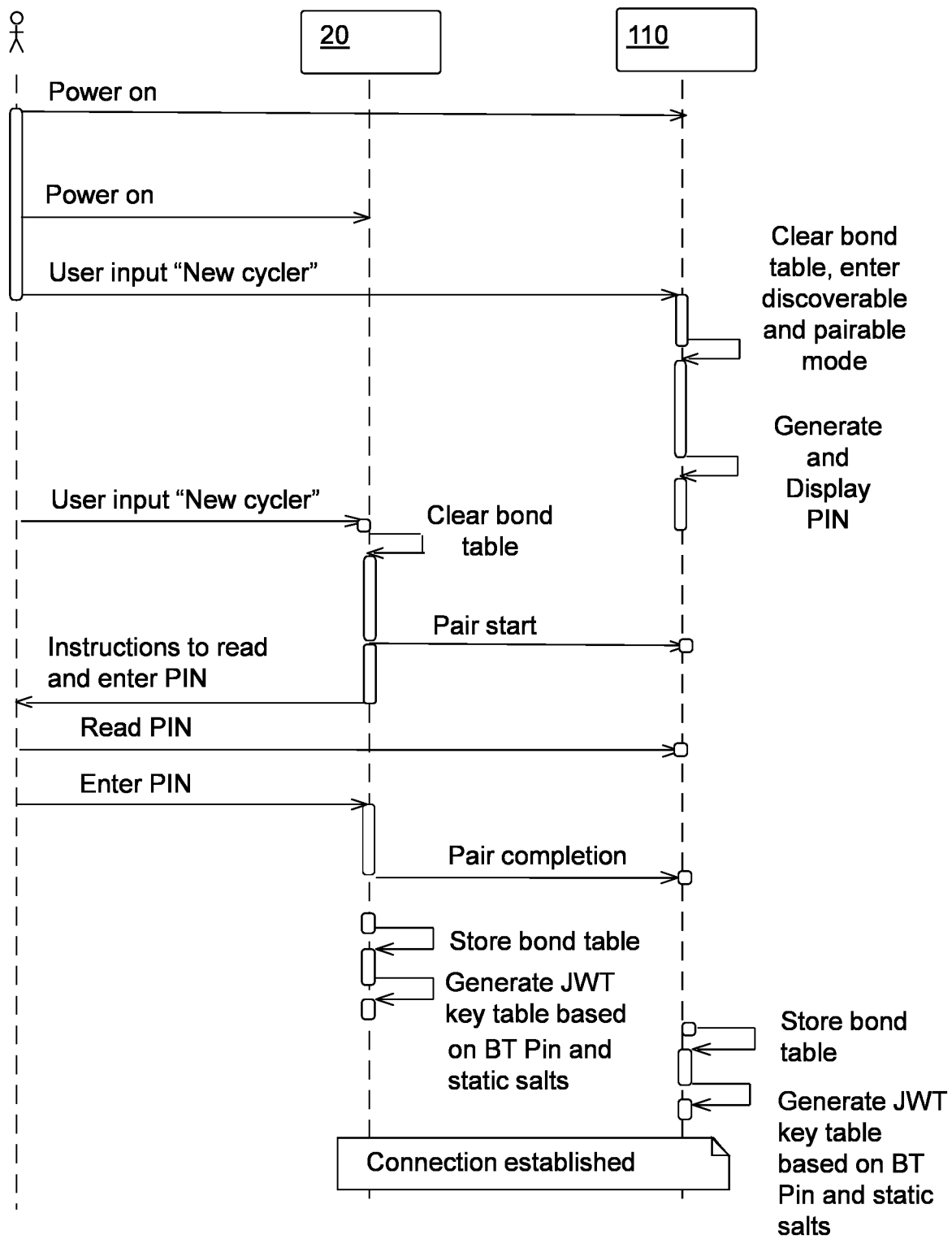

FIG. 7f illustrates an alternative implementation of the procedure for BT connect described in FIG. 7a. In contrast to the example of FIG. 7a, the pairing is in this implementation triggered by a user providing user input (e.g. a command "New Cycler") first at the water purifier 110, and then the user input may be entered e.g. at the cycler 20. The user input may be entered e.g. using a button, keypad or other user interface. Manual trigger of the pairing on both sides (i.e. both at the dialysis machine and the water purifier) may be considered more secure as it is user controlled.

The water purifier 110 will in response to receiving this command clear its bond table and enter a discoverable mode. It will also generate a passkey (e.g. a PIN) and display the passkey on a display of the water purifier 110.

The cycler 20, in response to receiving the command, also clears its bond table and initiates the standard BT pairing procedure by starting to scan for a BT beacon transmitted by the water purifier 110. In addition, the cycler 20 will provide instructions to the user to "Read and enter PIN" (e.g. via a user interface such as a key board). Thus, the user is instructed to read the passkey displayed at the water purifier 110 and to input the passkey in the cycler 20. Once, the passkey is available at both sides, the standard BT pairing is completed according to the standard procedure and the JWT key table to use when establishing the secure connection is then generated. Thus, from the steps of reading and entering the PIN, the method is similar to the corresponding steps in FIG. 7a. The proposed methods or establishing a secure connection is then performed in the same manner as described in connection with e.g. FIGS. 7d and 7e.

It should be understood that various changes and modifications to the presently preferred embodiments described herein will be apparent to those skilled in the art. For example, it is possible that some of the method steps are performed in another order. Such changes and modifications can be made without departing from the spirit and scope of the present subject matter and without diminishing its intended advantages. It is therefore intended that such changes and modifications be covered by the appended claims.

The invention claimed is:
1. A dialysis machine comprising:
a short-range communication interface;
a memory; and
a control unit configured to cause the dialysis machine to
  establish, using the short-range communication interface, a short-range wireless connection between the dialysis machine and medical equipment by:
    receiving, via a user interface, a passkey associated with the medical equipment,
    using the passkey to pair with the medical equipment,
    creating a new bonding table or writing to an empty bonding table using the passkey,
    generating a shared key using the passkey and at least one predetermined criterion, wherein the medical equipment separately has its own shared key,
    storing the shared key to a key table in the memory,
    using the shared key to authenticate with the medical equipment, and
    when authentication with the medical equipment is successful, enabling data communication using the short-range wireless connection with the medical equipment.
2. The dialysis machine of claim 1, wherein the medical equipment includes a water purifier, a blood pressure monitor, or a scale.
3. The dialysis machine of claim 1, wherein the short-range communication interface is configured with at least one of a Bluetooth™ protocol, a WiFi™ protocol, a Zigbee® protocol, a Z-Wave® protocol, a wireless Universal Serial Bus protocol, or an infrared protocol.
4. The dialysis machine of claim 1, wherein the control unit is further configured to:

after being powered on, determine whether the bonding table exists in the memory or whether the bonding table is empty; and when the bonding table does not exist in the memory or is empty, cause the user interface to display a prompt for entering the passkey associated with the medical equipment.

5. The dialysis machine of claim 4, wherein the control unit is further configured to, when the bonding table exists in the memory with the passkey, skip authentication and enable the data communication using the short-range wireless connection with the medical equipment.

6. The dialysis machine of claim 1, wherein the at least one predetermined criterion includes at least one of an algorithm or a cryptographic salt such that the passkey is an input parameter to the at least one predetermined criterion.

7. The dialysis machine of claim 1, wherein generating the shared key includes generating a set of shared keys using the passkey and the at least one predetermined criterion, and wherein the control unit is further configured to:
select a shared key from the set of shared keys;
obtain an identifier corresponding to the selected shared key; and
transmit the identifier and the shared key to the medical equipment for authentication with the medical equipment.

8. The dialysis machine of claim 7, wherein the identifier includes an index number of the selected shared key within the key table, and
wherein the control unit is further configured to select the shared key randomly from the set of shared keys.

9. The dialysis machine of claim 1, wherein the memory is configured to store an identifier of the dialysis machine, and wherein authenticating with the medical equipment includes transmitting an authentication request message including the shared key and the identifier of the dialysis machine to the medical equipment.

10. The dialysis machine of claim 9, wherein the control unit is further configured to determine at least one of (i) a system time, (ii) a generation time of the authentication request message, or (iii) an expiry time of the authentication request message, and wherein the control unit is configured to include at least one of (i) to (iii) within the authentication request message.

11. The dialysis machine of claim 9, wherein the control unit is further configured to:
generate a cryptographic signature using the passkey and at least some of the information included within the authentication request message; and
transmit the cryptographic signature in conjunction with the authentication request message.

12. The dialysis machine of claim 11, wherein the control unit is further configured to:
receive an authentication accept message from the medical equipment, the authentication accept message including at least a second cryptographic signature; and
determine authentication is successful after using the second cryptographic signature to verify authenticity of the medical equipment.

13. The dialysis machine of claim 1, wherein the control unit is configured to authenticate with the medical equipment using a JSON Web Token authentication protocol.

14. A dialysis system comprising:
medical equipment having a first short-range communication interface, a first memory storing a passkey, and a shared key generated using the passkey and at least one predetermined criterion; and a dialysis machine including a second short-range communication interface, a second memory, and a control unit, wherein the control unit of the dialysis machine is configured to cause the dialysis machine to establish, using the second short-range communication interface, a short-range wireless connection between the dialysis machine and the medical equipment by:
after being powered on, determining whether a bonding table exists in the second memory or whether a bonding table is empty,
when the bonding table does not exist in the second memory or is empty, causing a user interface of the dialysis machine to display a prompt to enter the passkey associated with the medical equipment,
receiving, via the user interface, the passkey,
using the passkey to pair the dialysis machine with the medical equipment,
creating a new bonding table or writing to an empty bonding table in the second memory using the passkey,
generating the shared key using the passkey and the at least one predetermined criterion,
storing the shared key to a key table in the second memory,
using the shared key to authenticate with the medical equipment, and
when authentication with the medical equipment is successful, enabling data communication using the short-range wireless connection with the medical equipment.

15. The dialysis system of claim 14, wherein the medical equipment includes a display and an input device.

16. The dialysis system of claim 14, wherein the dialysis machine is configured to receive data from the medical equipment after the data communication is enabled.

17. The dialysis system of claim 14, wherein the dialysis machine includes at least one of a peritoneal dialysis cycler, a hemodialysis machine, or a continuous renal replacement therapy ("CRRT") machine.

18. The dialysis system of claim 14, wherein the medical equipment is configured to display the passkey after being powered on and determining a bonding table does not exist in the first memory or a bonding table is empty.

19. The dialysis system of claim 14, wherein the at least one predetermined criterion includes at least one of an algorithm or a cryptographic salt such that the passkey is an input parameter to the at least one predetermined criterion.

20. The dialysis system of claim 14, wherein generating the shared key includes generating a set of shared keys using the passkey and the at least one predetermined criterion, and wherein the control unit of the dialysis machine is further configured to:
select a shared key from the set of shared keys;
obtain an identifier corresponding to the selected shared key; and
transmit the identifier and the shared key to the medical equipment for authentication with the medical equipment.

21. The dialysis system of claim 14, further comprising second medical equipment having a third short-range communication interface, a third memory storing a second passkey, and a second shared key generated using the second passkey and the at least one predetermined criterion or a second predetermined criterion,
wherein the control unit of the dialysis machine is configured to cause the dialysis machine to establish, using the second short-range communication interface, a second short-range wireless connection between the dialysis machine and the second medical equipment by:
causing the user interface of the dialysis machine to display a second prompt to enter the second passkey associated with the second medical equipment,
receiving, via the user interface, the second passkey,
using the second passkey to pair the dialysis machine with the second medical equipment,
updating the bonding table in the second memory using the second passkey,
generating the second shared key using the second passkey and the at least one predetermined criterion or the second predetermined criterion,
storing the second shared key to the key table in the second memory,
using the second shared key to authenticate with the second medical equipment, and
when authentication with the second medical equipment is successful, enabling data communication using the second short-range wireless connection with the second medical equipment.

* * * * *